(12) United States Patent
Litton

(10) Patent No.: US 9,980,880 B1
(45) Date of Patent: May 29, 2018

(54) PILL DISPENSER WITH COMPLIANCE FEATURES

(71) Applicant: Linda Jean Litton, Scottsdale, AZ (US)

(72) Inventor: Linda Jean Litton, Scottsdale, AZ (US)

( * ) Notice: Subject to any disclaimer, the term of this patent is extended or adjusted under 35 U.S.C. 154(b) by 0 days. days.

(21) Appl. No.: 15/442,675

(22) Filed: Feb. 26, 2017

Related U.S. Application Data

(63) Continuation of application No. 14/485,371, filed on Sep. 12, 2014, now Pat. No. 9,579,264.
(60) Provisional application No. 61/877,807, filed on Sep. 13, 2013.

(51) Int. Cl.
| | | |
|---|---|---|
| *A61J 7/00* | (2006.01) | |
| *A61J 7/04* | (2006.01) | |
| *G07F 17/00* | (2006.01) | |
| *G06F 19/00* | (2018.01) | |

(52) U.S. Cl.
CPC .......... *A61J 7/0084* (2013.01); *A61J 7/0436* (2015.05); *A61J 7/0481* (2013.01); *G06F 19/3462* (2013.01); *G07F 17/0092* (2013.01); *A61J 2200/30* (2013.01)

(58) Field of Classification Search
CPC ....... A61J 7/0454; A61J 7/0481; A61J 7/0084
USPC ......................................................... 700/237
See application file for complete search history.

(56) References Cited

U.S. PATENT DOCUMENTS

| | | | | |
|---|---|---|---|---|
| 7,896,192 B2 * | 3/2011 | Conley | ................. | A61J 7/0472 221/15 |
| 8,391,104 B2 * | 3/2013 | de la Huerga | .......... | A61J 1/035 206/459.5 |
| 9,443,370 B2 * | 9/2016 | Carson | ..................... | G07F 9/006 |
| 9,501,887 B2 * | 11/2016 | Berg | ....................... | G07F 11/005 |
| 2002/0147526 A1 * | 10/2002 | Siegel | .................... | A61J 7/0481 700/237 |
| 2006/0213921 A1 * | 9/2006 | Abdulhay | ............. | A61J 7/0084 221/130 |
| 2006/0259187 A1 * | 11/2006 | Berg | ....................... | G07F 9/026 700/231 |
| 2006/0259188 A1 * | 11/2006 | Berg | ..................... | A61J 7/0084 700/231 |
| 2007/0093932 A1 * | 4/2007 | Abdulhay | ............. | A61J 7/0084 700/231 |

(Continued)

FOREIGN PATENT DOCUMENTS

WO   WO -2008010989 A1 *   1/2008   ............ A61J 7/0481

*Primary Examiner* — Patrick Cicchino
(74) *Attorney, Agent, or Firm* — Invention to Patent Services; Alex Hobson

(57) ABSTRACT

A pill dispenser is configured to receive a plurality of different pill types into discrete pill reservoirs, whereby a dose of different pills may be provided to a user in a dispense reservoir. A vacuum manifold may be configured with a vacuum tube for removing pills from the discrete reservoirs and placing them into the dispense reservoir. In one embodiment, a pill dispenser is part of a pill dispenser system that utilizes a remote electronic device having an application software program for setting, managing and displaying the dosing regimens for pills loaded into the pill dispenser. The application software program may be coupled with a prescribing pill database, whereby prescription pill information, including dosing regimens may be loaded onto the application software program to ensure compliance with the prescription.

14 Claims, 33 Drawing Sheets

(56) References Cited

U.S. PATENT DOCUMENTS

| | | | |
|---|---|---|---|
| 2007/0193225 A1* | 8/2007 | Bailey | A61J 3/06 53/281 |
| 2010/0220553 A1* | 9/2010 | Nurse | A61J 7/0481 368/10 |
| 2010/0256808 A1* | 10/2010 | Hui | G07F 7/025 700/225 |
| 2011/0166700 A1* | 7/2011 | Dunn | A61J 1/03 700/237 |
| 2013/0226339 A1* | 8/2013 | Ervin | G07F 17/0092 700/240 |

* cited by examiner

Prescription List

Load a Prescription

Select the Prescription you would like to add to Precise Meds

| Medication Name | Generic Name | Until Date |
|---|---|---|
| DioVan 320<br><br>2345678-05776 | | 5/16/2014 |
| Lovastatin 40 MG<br><br>2345678-05776 | | 9/23/2014 |
| Metformain 1000 MG<br><br>2345678-05776 | | 9/23/2014 |
| Famotidine 40 MG<br><br>12345678-1234 | | 11/22/2014 |
| testing 2x weekly 2x daily<br><br>2222 | | 8/2/2014 |

FIG. 16

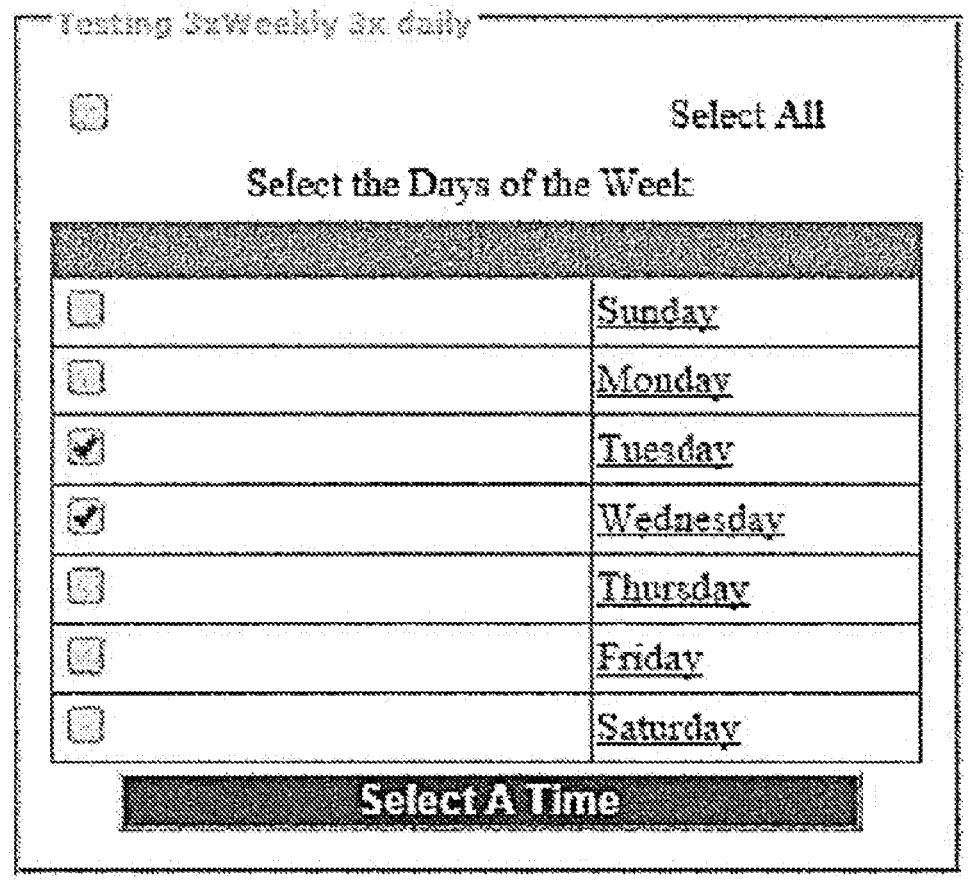
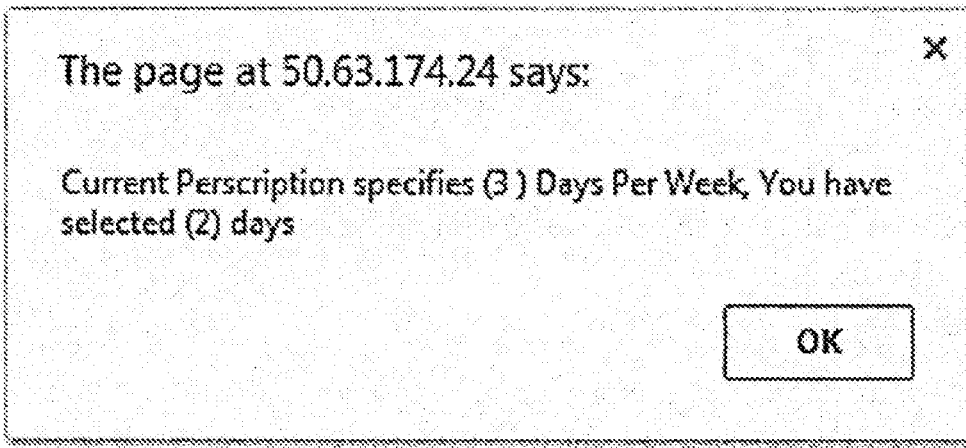
FIG. 17

Automated Pill Dispenser

| | Change Password | Logout: PreMeds |
|---|---|---|

≤ Back

Set Schedule List

| Prescription | WeekDay | Hours | Minutes | Time |
|---|---|---|---|---|
| Lovastatin 40 MG | Monday | 00 ▼ | 00 ▼ | AM ▼ |

Load Machine

Current Shedule List

| Prescription | WeekDay | Time |
|---|---|---|
| Famotidine 40 MG | Monday | 08:15 AM |
| DioVan 320 | Monday | 08:15 AM |
| Default Time 1 | Monday | 09:00 AM |
| Default Time 2 | Monday | 12:01 PM |

Precise Meds

The Precise Meds machine is ready to load now

Click OK once you are complete.

| OK |
|---|

FIG. 19

≤ Back

Prescription List

| Medicine | ○ Prescription ● Non Prescription |

Description: Vitamin C

Dosage Take: 1 Tablets/Pills

Dosage Times: 1

Dosage Period: Daily ▼

Daily
1 x Weekly
2 x Weekly
3 x Weekly
4 x Weekly
5 x Weekly
6 x Weekly

Total Quantity:

Until Date:

Refills: 0

Instruction:

Save        Delete        Cancel

FIG. 20

< Back

Pill Supply

| Prescription |
|---|
| Testing 3xWeekly 3x daily (3 Times Daily) |
| Famotidine 40 MG (1 Times Daily) |
| DioVan 320 (1 Times Daily) |
| Metformain 1000 MG (2 Times Daily) |
| Lovastatin 40 MG (1 Times Daily) |

FIG. 21

≤ Back

Pill Supply Detail

Precise Meds
VIEW Pill Supply Details

Expires on: This Prescription Expires on 7/31/2015

RX#: 11111111

Medication Name: DiaVan 320

Generic Name:

Remaining: 2

Refills: 2

Unitl Date: 7/31/2015

Load Date: 7/20/2014

Instructions:

Take with food.

< Back

| Prescription | WeekDay | Hours | Minutes | Time |
|---|---|---|---|---|
| Famotidine 40 MG | Sunday | 8 | 15 | AM |
| DioVan 320 | Sunday | 8 | 15 | AM |
| DioVan 320 | Monday | 8 | 15 | AM |
| Famotidine 40 MG | Monday | 8 | 15 | AM |
| Famotidine 40 MG | Tuesday | 8 | 15 | AM |
| DioVan 320 | Tuesday | 8 | 15 | AM |
| testing 2x weekly 2x daily | Tuesday | 8 | 15 | AM |
| testing 2x weekly 2x daily | Tuesday | 1 | 00 | PM |
| testing 2x weekly 2x daily | Wednesday | 8 | 15 | AM |
| DioVan 320 | Wednesday | 8 | 15 | AM |
| Famotidine 40 MG | Wednesday | 8 | 15 | AM |
| testing 2x weekly 2x daily | Wednesday | 1 | 00 | PM |
| Famotidine 40 MG | Thursday | 8 | 15 | AM |

Update Schedule

FIG. 23

≤ Back

Prescription List

Reset\UnLoad Pills

Select the Prescription you would like to Remove

| Medication Name |
|---|
| DioVan 320  <br> 2345678-05776 |
| Lovastatin 40 MG  <br> 2345678-05776 |
| Metformain 1000 MG  <br> 2345678-05776 |
| Famotidine 40 MG  <br> 12345678-1234 |
| Testing 3xWeekly 3x daily  <br> 1234 |

FIG. 24

PILL DISPENSER WITH COMPLIANCE FEATURES

CROSS REFERENCE TO RELATED APPLICATIONS

This application is a continuation of U.S. patent application Ser. No. 14/485,371, filed on Sep. 12, 2014 and currently pending, which claims the benefit of U.S. Provisional Patent Application No. 61/877,807, filed on Sep. 13, 2013 and entitled Pill Dispenser and Dispensing System Utilizing a Remote Electronic Scheduler; the entirety of both applications are incorporated by reference herein.

BACKGROUND OF THE INVENTION

Field of the Invention

The present invention relates to automatic pill dispensers.

Background

Pharmaceutical companies have developed a wide range of pills to treat or prevent any number of different ailments and conditions. Many people, especially the elderly are prescribed many different pills to take throughout the day. In addition, supplements have grown in popularity in recent years and many people are taking an assortment of non-prescription supplements. Keeping track of all of these pills can be difficult and time consuming. In some case, taking the wrong dose or missing a dose can lead to poor health or an emergency situation.

Pill organizers, having a plurality of compartments typically labeled with a day of the week and/or time of day, provide some organization for a plurality of pills but require manual sorting which allows for human error and may result in non-compliance of the dosing regimen. Furthermore, some non-prescription pills or supplements may have a non-desirable interactions with a prescribed pill, and pill organizers provide no means to alert the user.

Pill organizers also provide no protection from theft of the medications, whereby some prescription pills may be removed from the pill reservoirs without the knowledge of the intended pill taker. Some narcotics, and especially opiates for example, have become a major addiction problem, especially with teenagers. Prescribed medications are routinely stolen to feed their addition.

There are any number of electronic pill dispensers, available and most of them require pills to be manually sorted into compartments or require the pills to be provided in a prepackaged form that can be properly received by the pill organizer and/or dispenser. These types of pill dispensers do not provide a means to confirm the proper pill was loaded into an appropriate reservoir which can lead to non-compliance with the dosing schedule for one or more pills.

Many family members and caregivers not residing with a user/patient required to take any number of pills, worry about compliance to a dosing regimen. In many cases, they are forced to check in on the patient to ensure that they are complying with the dosing regimen.

There exists a need for a pill dispenser that allows a user to load a plurality of pills, each into their own reservoir, whereby pills may be removed from the reservoirs and provided to the user at appropriate dosing times.

There exists a need for a pill dispenser that can interface with scheduling software to confirm that the proper pill was loaded into a reservoir.

There exists a need for a pill dispenser that can interface with scheduling software to alert the user of an interaction between a pill to be loaded and one in the dispenser.

There exists a need for a pill dispenser or pill dispenser system that can alert the user that a dose is ready through a remote electronic device.

There exists a need for a pill dispenser system that can alert a caregiver, or other alert contact, by an email, text, or phone call, if a dose has not been taken for a preset alert time.

There exists a need for a pill dispenser system that can interface with a scheduling software that is linked with a prescribing pill database.

There exists a need for a pill dispenser system that can compare dosing schedules for a given pill with a prescription dosing regimen to ensure compliance.

There exists a need for a pill dispenser system that can check and track compliance of dosing with scheduling software and provide a report on compliance with the dosing schedule.

There exists a need for a pill dispenser that can interface with scheduling software that is run on a remote electronic device, such as a mobile phone.

There exists a need for a pill dispenser that can receive and confirm loading of prescribed pills and also receive a non-prescribed pill and inform the user of any side-effects.

There exists a need for a pill dispenser that can keep track of the quantity and type of pills within the dispenser and display this information to a user through a remote electronic device.

There exists a need for a pill dispenser that can keep back of and provide a report of non-compliance events.

There exists a need for a pill dispenser that can automatically update a dosing regimen based on a missed dose or non-compliance.

There exists a need for a pill dispenser that can dispense pills when needed, such as non-prescription pills and prescription pills with a "take as needed" dosing prescription.

There exists a need for a pill dispenser that retains the pills in an enclosure having a door that can lock, whereby a user can open the door by inputting a password. This type of pill dispenser would prevent theft of medications from the dispenser.

It is therefore the objective of this invention to provide a pill dispenser and dispensing system that meets any combination of the above needs.

SUMMARY OF THE INVENTION

The invention is directed to a pill dispenser that is configured to receive a plurality of different pill types, whereby each pill type can be simply loaded into a pill reservoir and automatically dispensed therefrom. The pill dispenser also comprises a dispense reservoir for receiving a variety of pills from the individual pill reservoirs to provide a dose to a user. A vacuum manifold may be configured with a vacuum tube having a collection tip for removing pills from the individual reservoirs and placing them into a dispense reservoir.

The individual pill reservoirs may be configured on a turntable that is configured to spin, whereby each pill reservoir and dispense reservoir can be located under the vacuum tube for removal and placement respectively. The reservoirs may be wedge shaped, for example, and configured in a circular configuration, and in some embodiments, configured about a circular turntable. A reservoir may be any suitable shape and may have a plurality of sides and a base to form a volume for receiving pills through an open top. A pill reservoir may be generally triangular, square, rectangular, wedged shaped and the like. In one embodiment, the pill dispenser comprises a turntable having a plurality of reservoirs. In another embodiment, a dispense reservoir is configured with a first turntable and a second turntable. The first turntable may, be configured under the second turntable and the second turntable may be configured with an opening for access of the vacuum tip into the first, or lower, turntable. A dispense reservoir may be configured in either the first or second turntable, or configured separate from either turntable. Any number of reservoirs may be configured on a turntable, such as four or more, five or more, six or more, seven or more, eight or more, ten or more, twelve or more and any number between and including the number of reservoirs provided.

A pill dispenser may comprise an enclosure for the pill reservoirs and one or more dispense reservoirs. An enclosure may be configured with an opening to allow access to the various reservoirs. An enclosure opening may allow a pill reservoir to be removed from the enclosure for loading a pill or removing a dose from a dispense reservoir. An enclosure may have a separate opening for loading pills and a separate opening for receiving dispensed pills, or for access to a dispense reservoir. An opening in an enclosure may be configured with a door, or other closure feature, that may be configured to lock to prevent access to the pill reservoirs and dispense reservoir. In one embodiment, a door or closure feature is configured to open automatically when a confirmation is provided by a user to retrieve a dose from the dispense reservoir. An enclosure having a door may prevent unwanted access to the pills within the pill dispenser and eliminate theft or non-compliance.

In one embodiment, a pill is identified prior to loading it into an individual pill reservoir. The pill dispenser may comprise an instruction symbol scanner that is configured to read an instruction symbol, such a bar code or QSR symbol associated with a pill. For example, a prescription pill bottle or package may comprise an instruction symbol that may be read by the instruction symbol scanner prior to loading. A software program may prompt a user to load a prescribed pill and then prompt the user to confirm the prescription by scanning with an instruction symbol scanner. In this way, non-compliance and human, error may be reduced or eliminated. In many cases, a user may pick up two or more prescriptions at a time and it may be important to confirm which prescription is loaded into each individual pill reservoir.

An exemplary pill dispenser comprises a vacuum manifold that is configured to lower a vacuum tube down into one of the plurality of pill reservoirs to remove a pill from one of the pill reservoirs, and subsequently raise the vacuum tube, with a pill attached thereto, above the pill reservoir. The turntable may spin to locate the vacuum tube with the pill attached thereto, over a dispense reservoir, whereby the vacuum tube may place the attached pill in the dispense reservoir. The manifold may lower the vacuum tube into the dispense reservoir or simply release the pill. A vacuum manifold may alternatively be configured to move to locate the vacuum tube over a required reservoir for removal and/or placement of a pill therein. The pill dispenser may comprise a vacuum pump to, provide the vacuum needed for attachment of pills to the vacuum tube.

A pill dispenser, as described herein, may comprise an alarm feature comprising a speaker to produce an alarm to alert the user that a dose is ready. An alarm feature may comprise a light feature and/or a sound feature. A pill dispenser may comprise a light that is configured to blink or illuminate to alert a user that a dose is ready, for example. Likewise, a pill dispenser may, be configured to sound an audible alarm when a dose is ready for retrieval. A pill dispenser may comprise a display screen that can display any number of messages to a user, including the time, next dose time, type of pills included in a dose, the contents of the pill dispenser including the name and, quantity of pills, the instructions for a given pill and side-effects. A pill dispenser may comprise a dispenser user interface, whereby a user can operate some or all of the physical functions of the dispenser. A dispenser user interface may provide a password input feature that enables a user to operate other functions of the pill dispenser and/or open a door to access a dispense reservoir, for example. In still another embodiment, a pill, dispenser is configured with a wireless signal transmitter that is configured to send an alarm or alert to a user's remote electronic device, such as a mobile telephone. A pill dispenser may be configured to send a text message, make a phone call, or send an email to a user's electronic device to alert them that a dose is ready or has been missed, etc.

In an exemplary embodiment, the pill dispenser may comprise a dispenser control system that consists of a signal receiver such as a wireless signal receiver, a control circuit and micro-processor for activating commands received by the wireless signal receiver. A dispenser control system may interface with any number of sensors to perform physical functions of the pill dispenser. For example, a wireless signal may provide instructions/commands to the dispenser control system to dispense a pill from a first pill reservoir and two pills from second pill reservoir. The dispenser control system may then simply follow the commands to provide the required pills in the dispense reservoir. In this exemplary embodiment, the dispenser control system is simply a slave to the commands of the wireless signal from a remote electronic device and performs the physical functions as directed. A pill dispenser may have any number of sensors and actuators to control the motion of the elements to perform the tasks as directed. A reservoir sensor may be configured to identify the location of a reservoir. A vacuum sensor may be configured, to determine, vacuum pressure, thereby indicating if a pill has been attached to the vacuum tip. A door sensor may be configured to indicate the position of a door or closure feature, for example.

A pill dispenser may be configured to provide a dose, or one or more pills from the pill reservoirs, to a dispense reservoir. The pill dispenser may remove one pill from first pill reservoir and two pills from a second pill reservoir and place them in a dispense reservoir at a scheduled dosing time, for example. An alarm and/or light may be activated to inform the user that a dose is ready. A user may then simply remove the pill from the dispense reservoir and a sensor may identify that the dispense reservoir has been removed or that a door or closure feature has been opened, thereby indicating that the dose has been taken. A user may also have to confirm that they have taken the dose through an input to a user interface on the pill dispenser or a remote electronic device. In another embodiment, a user has to interface with a user interface to have access to the dose. For example, a user may have to simply press a confirm button to open a door or release the dispense reservoir. In still another embodiment, a user may have to input a password into a dispenser user interface to unlock a door to the dispense reservoir. Any of these actions may confirm that the dose was taken and this information may be relayed to a remote electronic device.

A remote electronic device may be any suitable type of electronic device that can run an application software program, as described herein. A remote electronic device includes, but is not limited to, a mobile phone, a laptop computer, a personal computer, a tablet computer and the like. A remote electronic device may be a mobile electronic device that is configured to be carried and operated by a person as they travel from one location to another.

A remote electronic device may be configured with an application software program that provides a remote user interface for setting a dosing regimen, for example. An application software program may have any number of sub-programs to provide proper interaction with the pill dispenser. A remote electronic device and the application software program configured thereon, may be linked with a database for receiving prescription related information. A prescription provider may provide the application software program and host a database for interfacing with the application software program. For example, a user may get their prescription from Joe's Pharmacy, and Joe's Pharmacy may provide an application software program that interfaces with the Joe's Pharmacy database. When a user picks up a new prescription from Joe's Pharmacy, the prescription information may be provided to the application software program through the database.

A remote electronic device may be used to confirm a prescription for loading into the pill dispenser. A user may input a prescription number or any other confirmation number into a remote electronic device, thereby confirming the prescription to be loaded. A remote electronic device may then be used to set a dosing regimen for a loaded pill. A user may be prompted, by the application software program to set times of day, or a dosing regimen, for a newly loaded pill. Default times may be quickly selected by a user or a dose time may be input. This new dose time may then be added to a default time for future use. For example, a dispenser user may pick up a prescription for an antibiotic that is prescribed to be taken three times a day. The dispenser user may use their mobile phone, having the application software program described herein, to confirm loading of the antibiotic in the pill dispenser. A dispenser user may open the application software program on their phone and see that the antibiotic is ready for loading. They may then scan the barcode on the antibiotic prescription bottle using the instruction symbol scanner on the pill dispenser. The pill dispenser may then open a door to a pill reservoir, or instruct the user to pour the antibiotic pills into a specific pill reservoir, as they may be numbered or otherwise labeled. The dispenser user may select the times of day or dose times they want to take the antibiotic. Default times may be 7:00 am, 12:30 pm and 6:00 pm. The dispenser user may have other pills already in the pill dispenser that are already scheduled to be dosed at these default times, making it more convenient for taking a plurality of pills at one time. When the next dose time arrives, the pill dispenser may automatically remove the required pills from the pill reservoirs and place them in a dispense, reservoir. This may occur prior to the dose time to ensure the pills are ready at the selected dose time. A wireless signal from the remote electronic device may prompt the pill dispenser to prepare the dose or the dosing schedule may be loaded into the pill dispenser control system and the pill dispenser may simply follow these loaded instructions within the data-file.

The pill dispenser may simply operate the physical functions of the dispenser whereby a physical function includes, but is not limited to, movement or spinning of a turntable, opening a door, actuating a vacuum tube, turning on a vacuum pump, activating an alarm, activating a light and the like.

A remote electronic device may provide a user input feature for inputting a password. This password may open a door to an enclosure, for example on the pill dispenser, and/or allow modifications of a dosing regimen. In addition, a remote electronic device may comprise an instruction symbol scanner that can be used to confirm a prescription before loading it into the pill dispenser.

In an exemplary embodiment, a pill dispenser is part of a pill dispenser system that is configured to provide doses of pills at scheduled times and ensures compliance with prescribed dosing schedules. An exemplary pill dispenser system comprises a pill dispenser, as described herein, and a remote electronic device having a wireless signal generator configured to send a wireless signal to the pill dispenser's wireless signal receiver, a prescription database interface and a remote user interface. A mobile phone, for example, may have an application software program that interfaces with a prescription database and has a user interface for managing dosing regimens of the pill dispenser. The pill dispenser may have a dispenser control system that only controls physical functions of the dispenser and the pill scheduling functions may be controlled in total by the remote electronic device. As described, the pill dispenser control system may follow dispensing commands and schedules as set by the remote electronic device and application program thereon. The application software program, or application program, may be provided by a prescription pill provider or pharmacy company, for example.

In one embodiment, the application software program comprises a "dispense now" sub-program that is configured to activate the dispenser control system to remove a take-as-needed pill from one of the plurality of pill reservoirs and place the take-as-needed pill in a dispense reservoir to produce a dose. The pill dispenser may further comprises a door, whereby activation of the "dispense now" sub-program unlocks the door to allow access to the dispense reservoir. As previously described, a user may be required to input a password into the remote user interface, or dispenser interface to unlock the door to allow access the dispense reservoir.

A pill dispenser system may comprise a "dose" sub-program that may interface with a scheduled regimen and a clock and calendar to dispense a dose when a dose is scheduled. When a scheduled regimen date and time, or some offset time therefrom, corresponds with the current calendar date and time, the pill dispenser may retrieve the appropriate pills for the scheduled dose and place them in the dispense reservoir. A data-file having the scheduled dose dates and times may be stored within the pill dispenser control system and doses may be provided to the dispense reservoir without any additional communication from a remote source. An offset time of five minutes prior to the scheduled regimen date and time may be implemented by the pill dispenser system to ensure the dose is ready for retrieval in the dose reservoir at the scheduled time. A user may then remove the dose from the dispense reservoir and take the dose. A pill dispenser system may alert a user that a schedule dose is now ready by any suitable method including one or more alarm features, including a noise emitted from the dispenser or a flashing light. In addition, a pill dispenser system may be configured to alert a user through a remote electronic device. A user may have to confirm that they are ready to retrieve the dose before the dispense reservoir door is opened or unlocked. A dispense reservoir door may open automatically after a user confirms that they are ready to retrieve the dose. A user may have to input a password, or hit confirm on an application software program on a mobile electronic device, for example, A pill dispenser may have a user input feature to allow a user to input a confirmation that they are ready to receive a dose. After a dose has been removed, the dispenser reservoir door may automatically shut.

In one embodiment, the application software program comprises a "load prescription" sub-program that is configured to allow a user to load a plurality of discrete prescription pills into a pill reservoir, whereby the type of prescription pill loaded in a pill reservoir is confirmed by the application software program. The application software program may provide a prescription name, such as by displaying the prescription name on a remote electronic device, that is ready to be loaded into the pill dispenser. A user may then select the prescription name and input dosing times for that prescription and load the prescription pills into a pill reservoir whereby, the type of prescription pill loaded into a pill reservoir is confirmed by the application software program. When a plurality of prescriptions are picked up from a pharmacy, all of the prescription names may be displayed to the user and they may select one for loading. The dosing regimen for a prescription to be loaded may be automatically loaded into the application software program, whereby a user simply has to select the dosing times and days of the week. A prescription may require dosing three times a day, two times a day or one time a day, for example. The pill dispenser system may assure compliance with a dosing regimen by only allowing a scheduled regimen input that complies with the dosing regimen for the pill. A dosing regimen is a schedule that defines the quantity of pills and times for a pill to be taken and particularly a prescription pill. A dosing regimen may define that two pills be taken daily, for example. As described herein, a dosing regimen may be provided by a prescription pill provided through a database, an application software, an identification code on the prescription pill bottle or packaging, for example.

In one embodiment, the application software program comprises a non-prescription pill sub-program that is configured to allow entry of a pill type and dosing regimen. This sub-program may be used to load supplements or other non-prescription pills into the pill dispenser.

In one embodiment, the application software program comprises a "pill supply" sub-program that is configured to display the name of a pill loaded into one of the plurality of pill reservoirs and the quantity remaining, for example. The "pill supply" sub-program may be configured to display the contents of the pill dispenser including the pill names or generic names and quantity of pills in each pill reservoir and the pills in the dispense reservoir. The "pill supply" sub-program may also be configured to display a dosing schedule for a pill loaded into one of the plurality of pill reservoirs. The "pill supply" sub-program may also be configured to display a loaded date, a remaining pill count, refill quantity, or refill date for a pill loaded into one of the plurality of pill reservoirs. The "pill supply" sub-program may also be configured to display a prescription number and or instructions and side-effects for a pill loaded into one of the plurality of pill reservoirs.

In one embodiment, the application software program comprises a "change/view pill schedule" sub-program that is configured to show a dispensing schedule for a pill loaded into one of the plurality of pill reservoirs. The "change/view pill schedule" sub-program may be configured to allow modification of a dispensing schedule by a user on the remote device. Changing the dispensing schedule changes the scheduled regimen and any changes may be subject to compliance with a dosing regimen received from a remote source, such as a prescription provider.

In one embodiment, the application software program comprises a reset/unload pills sub-program configured to allow a user to unload one of the plurality of pill reservoirs. A user may be required to input a password into a user interface to unlock a door to have access to one the plurality of pill reservoirs under this sub-program.

In one embodiment, the application software program comprises a "view alarms" sub-program that is configured to display at least one alarm time and, allow a user to set at least one alarm time. An alarm time is a time of day when the pill dispenser may activate a sound alarm, or activate a light on the pill dispenser to alert the user that a dose is ready or should be taken soon.

In one embodiment, the application software program comprises an "alert" sub-program that is configured to send a notification of non-compliance when a dosage has not been taken per the dosing schedule. An alert notification may be a text message or call to a remote electronic device and it may be configured to be sent to the user of the pill dispenser and/or one or more alert contacts. An alert sub-program may be configured to display at least one alert time for at least one pill loaded into a pill, reservoir, whereby an alert will be automatically sent to a selected alert contact if the alert time has elapsed. An alert contact, may be selected from a contact list on the remote electronic device, for example. An alert time is a duration of time from the scheduled dispensing that may be set by a user on a user interface. An alert may be a text message, email, or phone call sent to an alert contact after an alert time has elapsed.

In one embodiment, the application software program comprises a "setting" sub-program that is configured to display at least one default time whereby a user may change or input a default time through a remote user interface. A plurality of default times may be displayed for selection. At least one default time may be displayed when selecting the dosing times in the "load prescription" sub-program.

In one embodiment, the application software program comprises "logout and/or login" sub-program configured to allow a mobile device user to logout or login to the application software program.

In one embodiment, the application software program is configured to provide an interaction alert if there are any potential harmful interactions between a pill loaded in the pill reservoirs of the pill dispenser and a pill to be loaded. The interaction alert may be configured to be displayed when a user is adding a pill to the dispenser under the "load a prescription" sub-program and the pill is identified by the application software program to have an interaction with a pill that is already loaded in the pill dispenser. The interaction alert may be configured to be displayed when a user is adding a pill to the dispenser under the "add a non-prescription pill" sub-program.

In one embodiment, the application software program comprises a "reporting" sub-program configured to record and track any non-compliance with a pill dosing regimen. The "reporting" sub-program may be configured to send a report to an alert contact if a pre-set number of non-compliance events occur. The reporting sub-program may be configured to keep track of all pills in the pill dispenser and their quantity.

The summary of the invention is provided as, a general introduction to some of the embodiments of the invention, and is not intended to be limiting. Additional example embodiments, including variations and alternative configurations of the invention, are provided herein.

BRIEF DESCRIPTION OF THE DRAWINGS

The accompanying drawings are included to provide a further understanding of the invention and, are incorporated in and constitute a part of this specification, illustrate embodiments of the invention, and together with the description serve to explain the principles of the invention.

DETAILED DESCRIPTION OF THE ILLUSTRATED EMBO EMBODIMENTS

Figure 1:
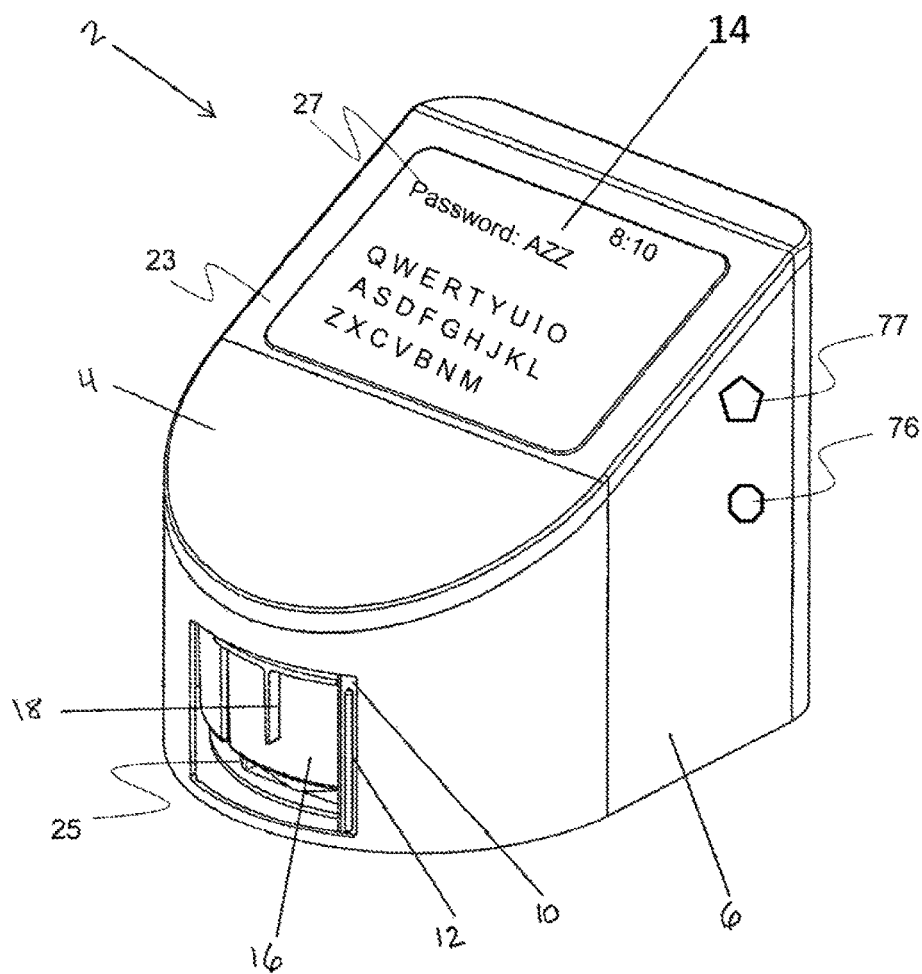

FIG. 1 shows n isometric view of an exemplary pill dispenser, as described herein.

Figure 2:
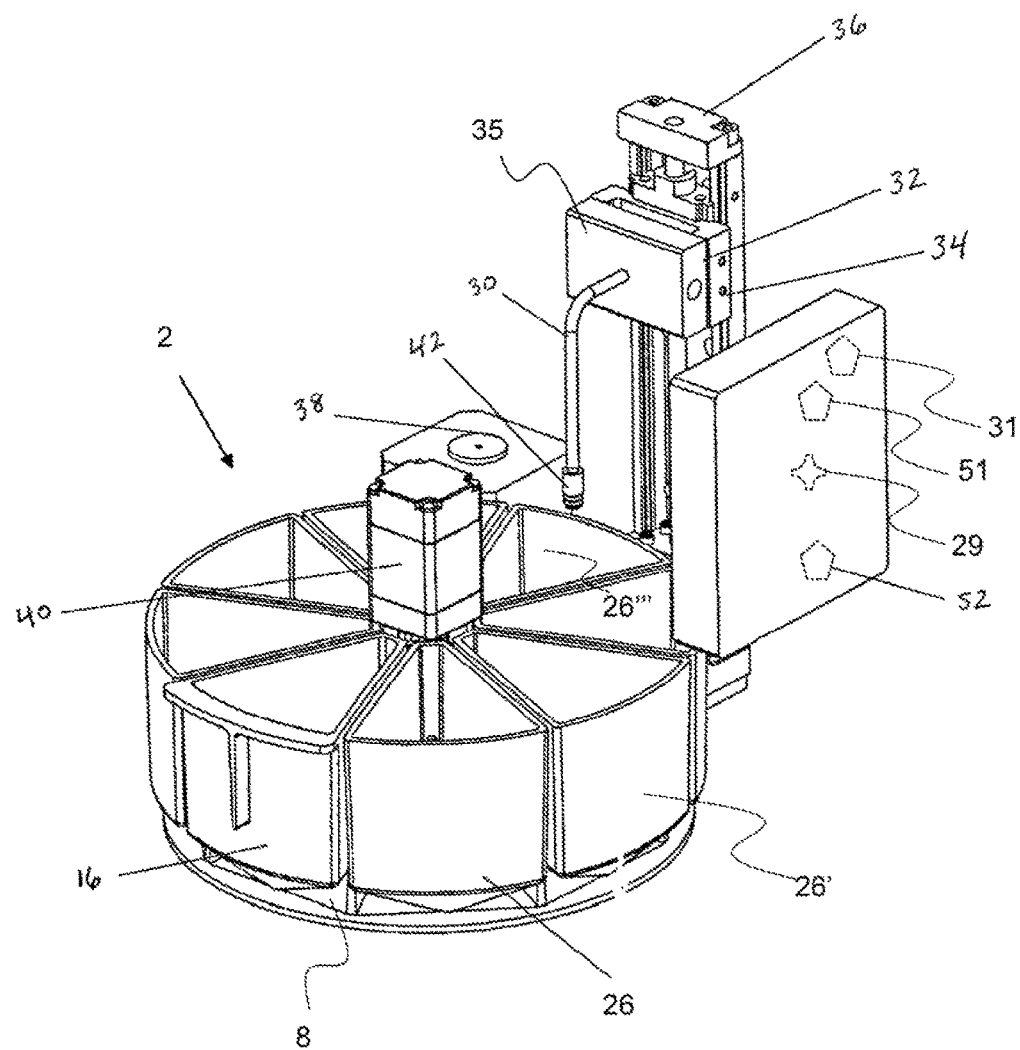

FIG. 2 shows an isometric view of an exemplary pill dispenser having a plurality of pill reservoirs configured on a turntable and a vacuum manifold, as described herein.

Figure 3:
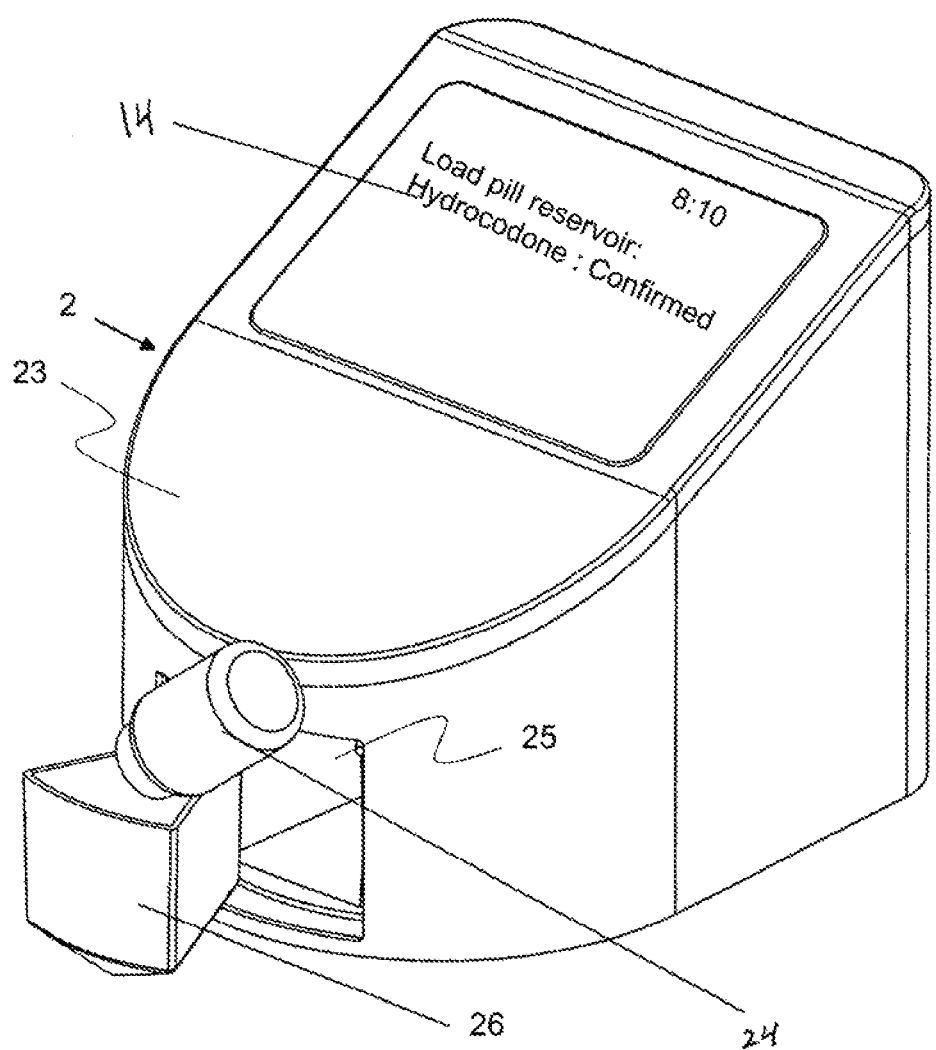

FIG. 3 shows an isometric view of an exemplary pill dispenser with a pill reservoir removed from the enclosure through an opening, as described herein.

Figure 4:
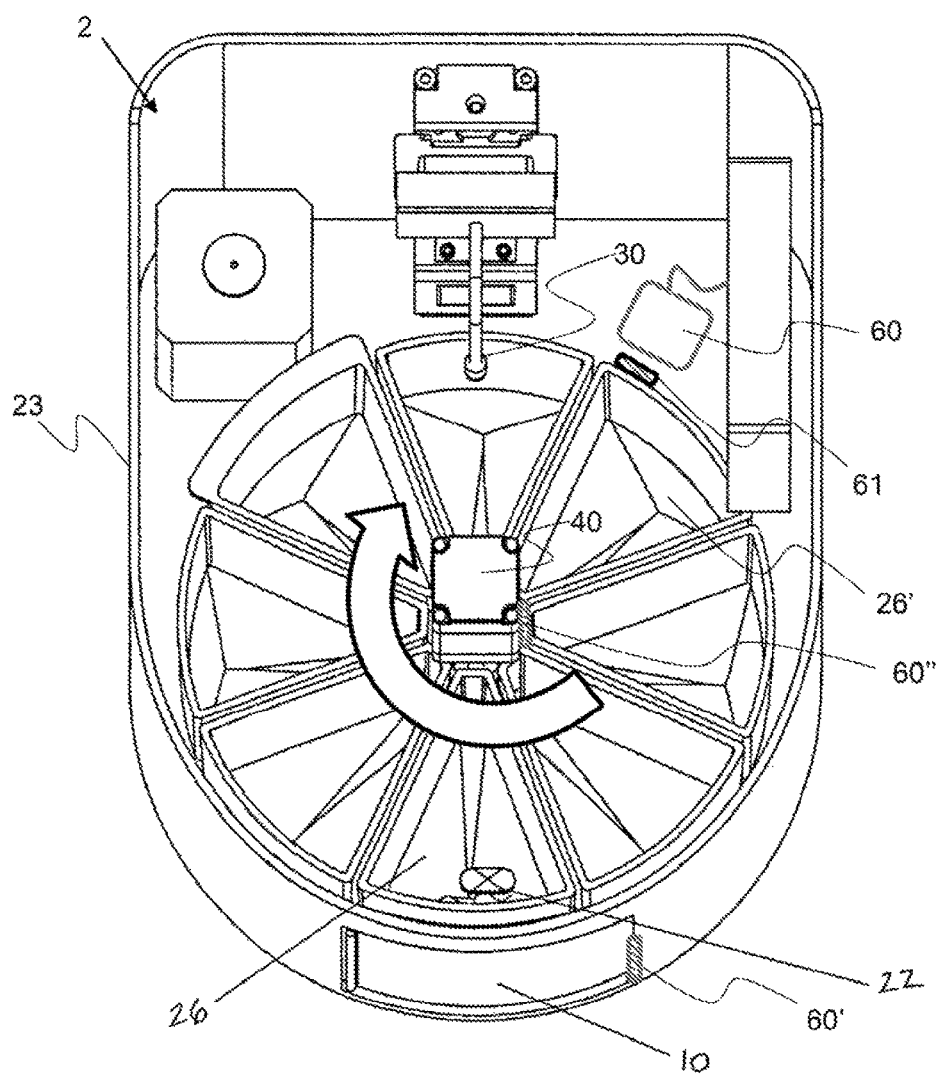

FIG. 4 shows a top-down view of the inside of an exemplary pill dispenser, as described herein.

Figures 5A, 5B:
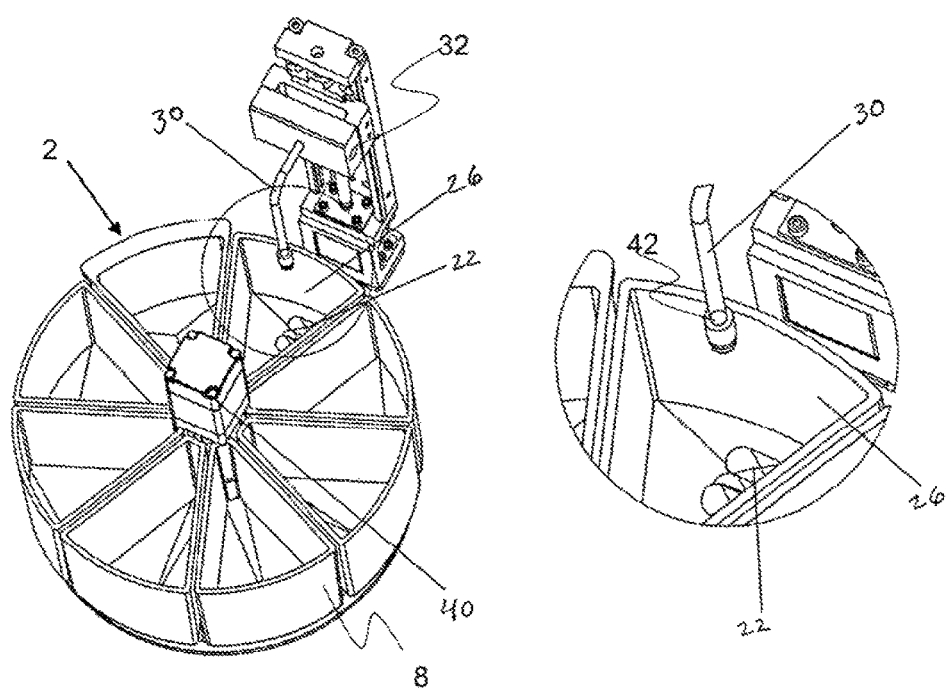

FIG. 5A shows a top-down isometric view of an exemplary pill dispenser having a vacuum tube coupled to a vacuum manifold.

FIG. 5B shows an enlarged top-down isometric view of a portion of the pill dispenser shown in FIG. 5A having a vacuum tube coupled to a vacuum manifold.

Figure 6A:
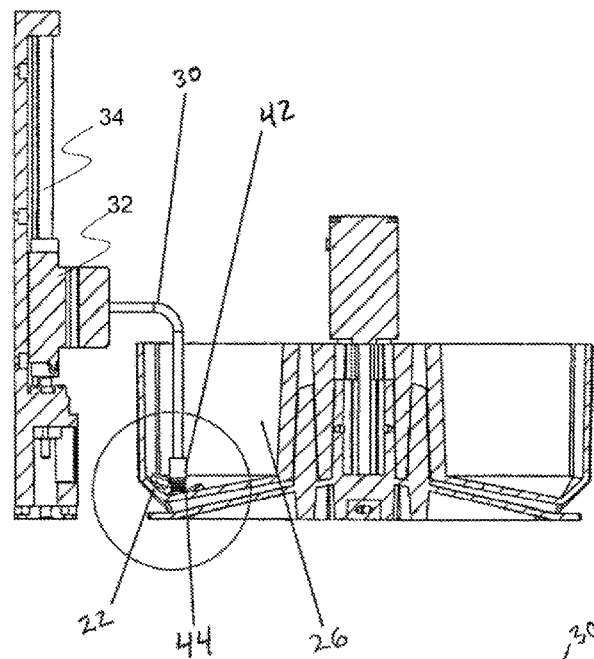

FIG. 6A shows a side cross-sectional view of an exemplary vacuum tube coupled to a vacuum manifold and in a down position with a pill reservoir.

Figure 6B:
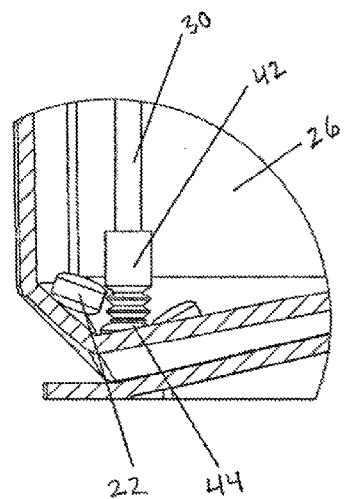

FIG. 6B shows an enlarged view of the vacuum tube shown in FIG. 6A attaching a pill to the vacuum tip.

Figure 7A:
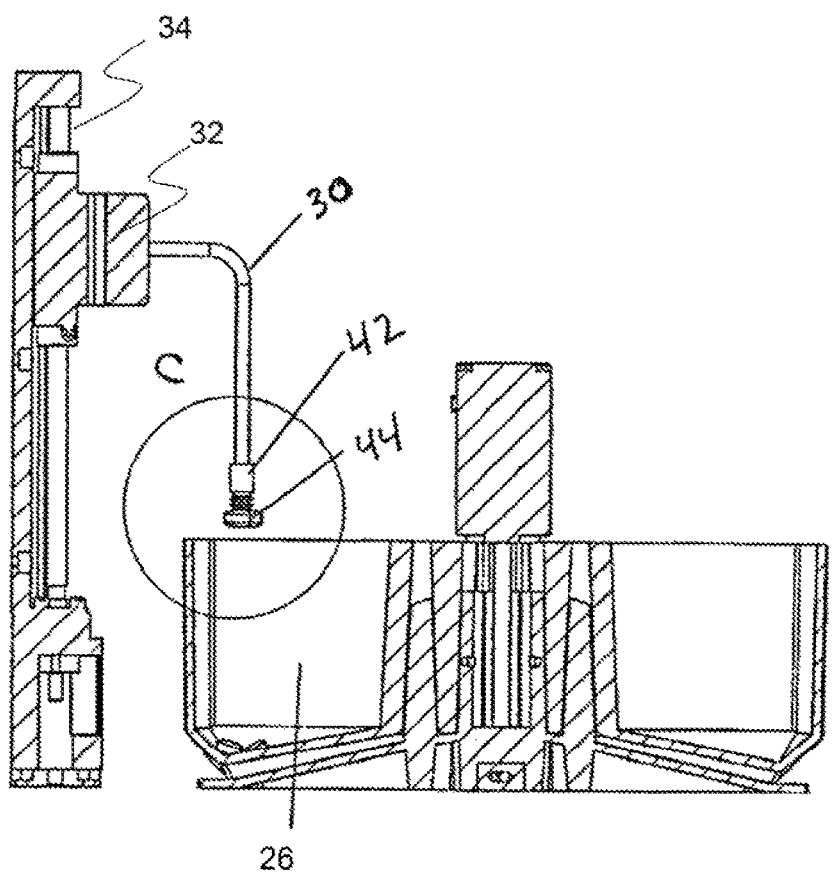

FIG. 7A shows a side cross-sectional view of an exemplary vacuum tube in an up position over a pill reservoir with a pill attached thereto.

Figure 7B:
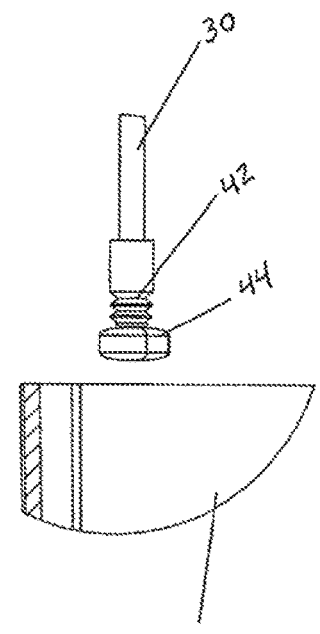

FIG. 7B shows an expanded view of the tube in FIG. 7A with a pill attached to the vacuum tip.

Figure 8:
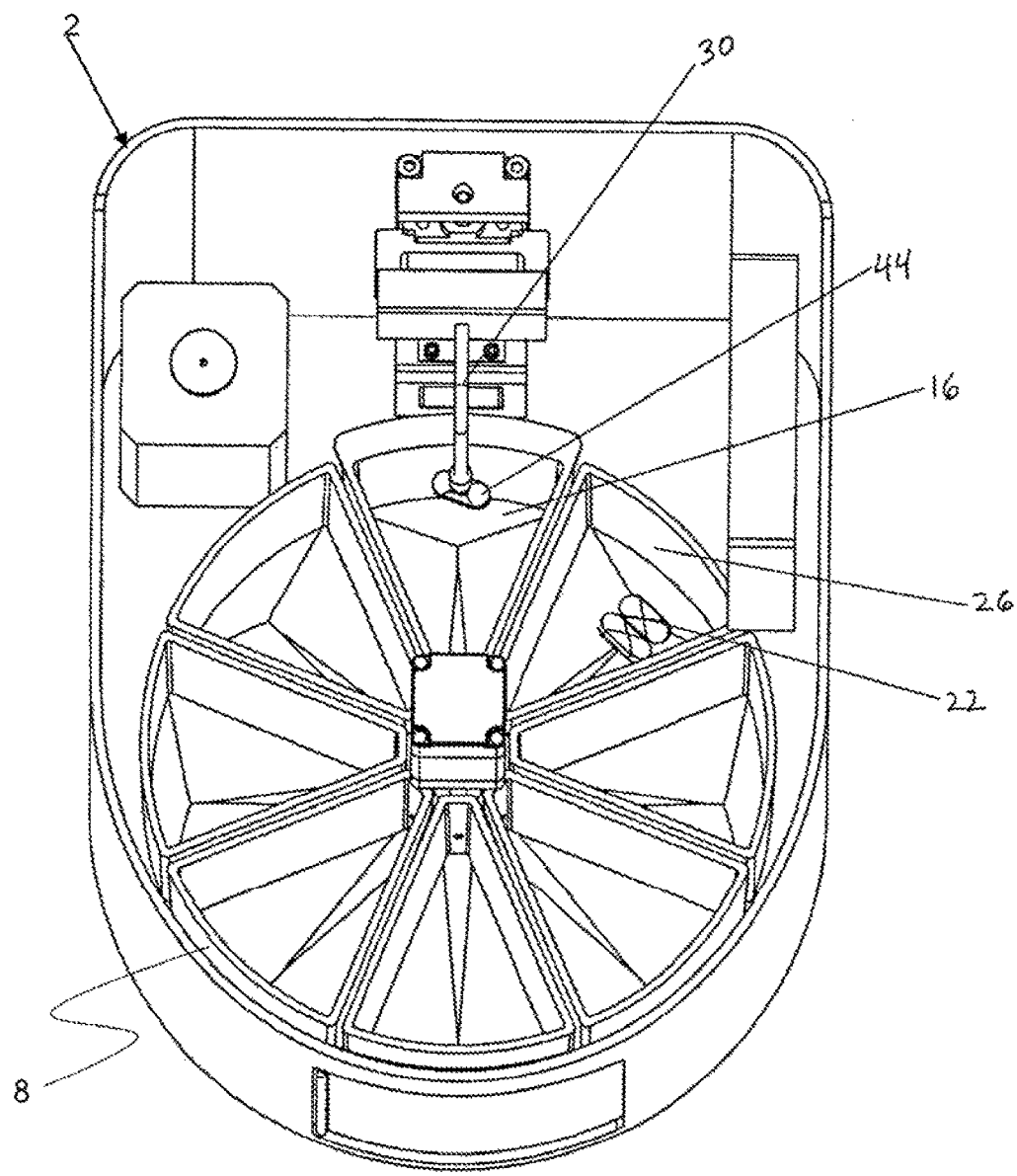

FIG. 8 shows a top-down view of an exemplary pill dispenser having a vacuum tube in an up position over a dispense reservoir.

Figure 9:
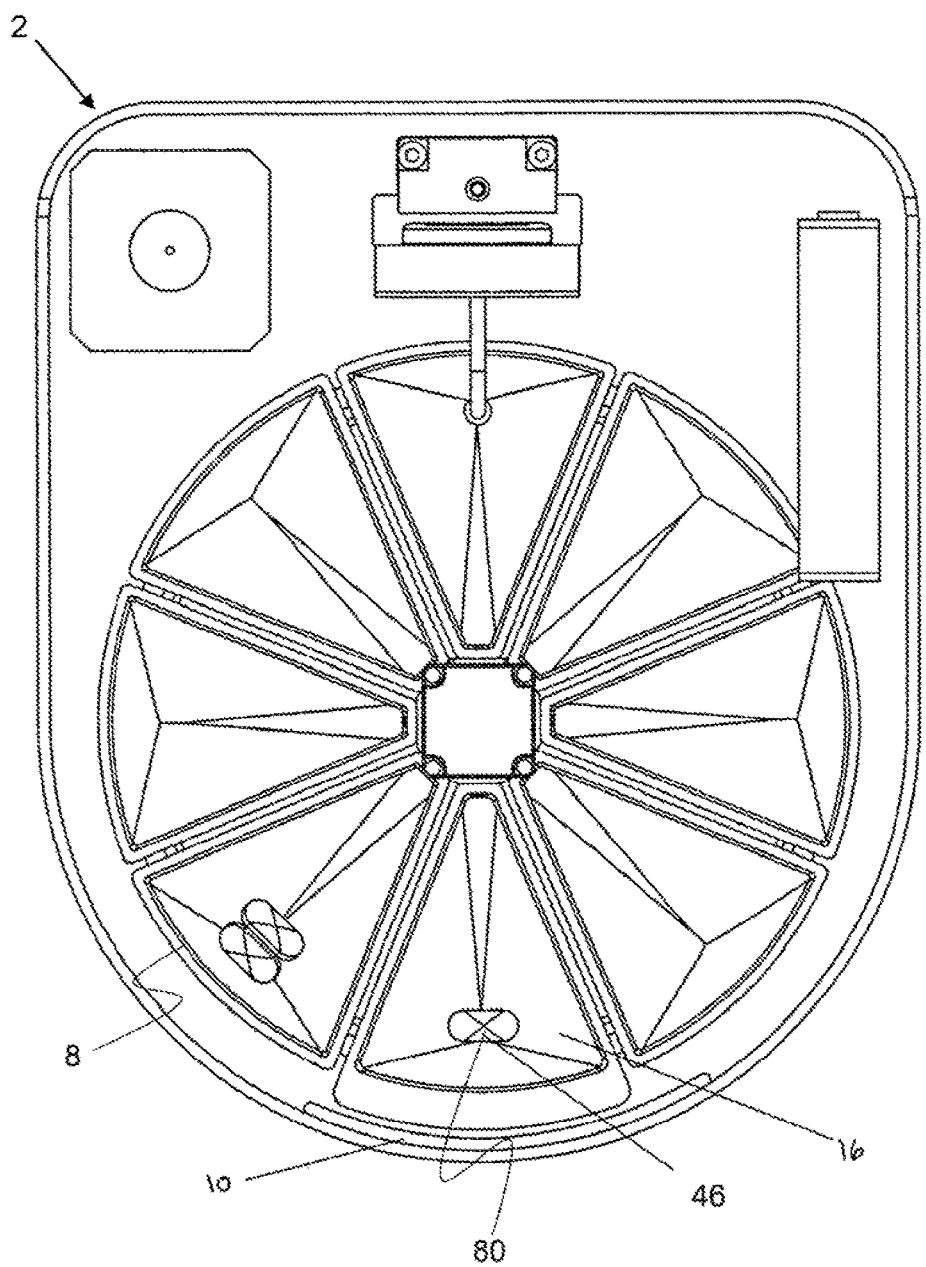

FIG. 9 shows a top-down view of an exemplary pill dispenser having a turntable configured with the dispenser reservoir aligned with the door location.

Figure 10:
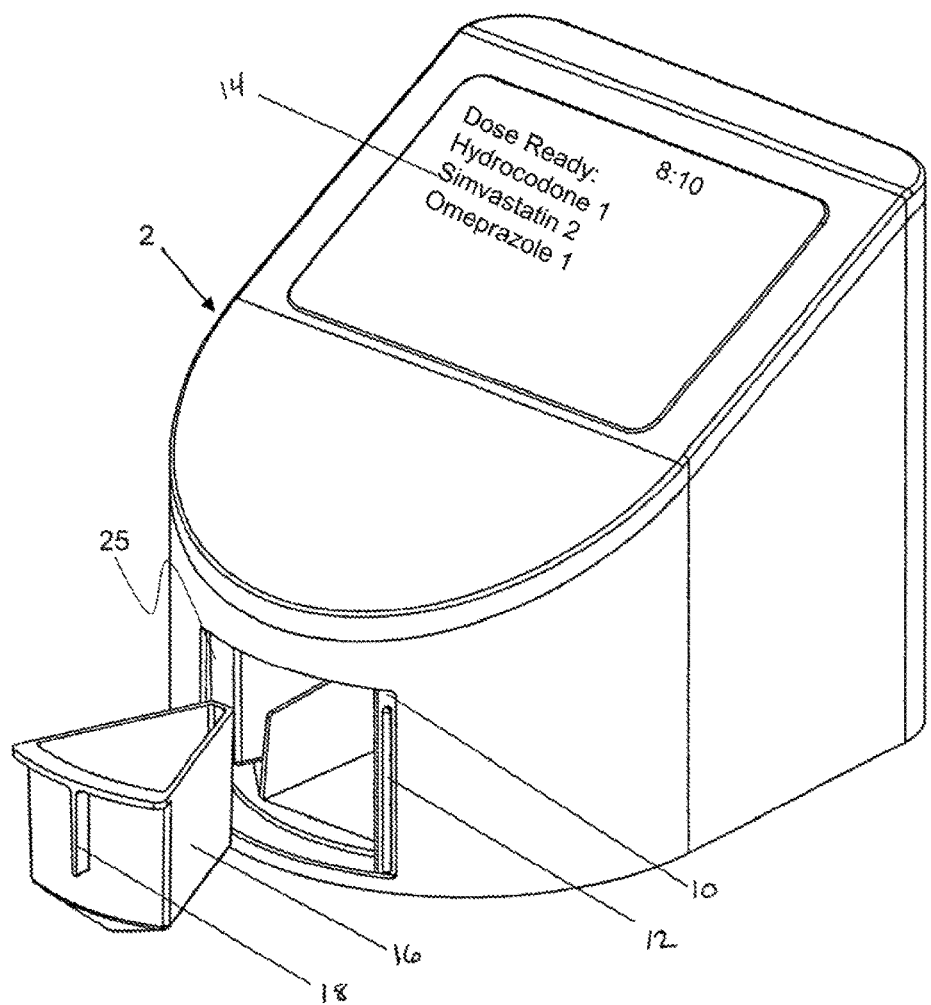

FIG. 10 shows an isometric view of an exemplary pill dispenser with a dispense reservoir removed from a dispenser opening.

Figure 11:
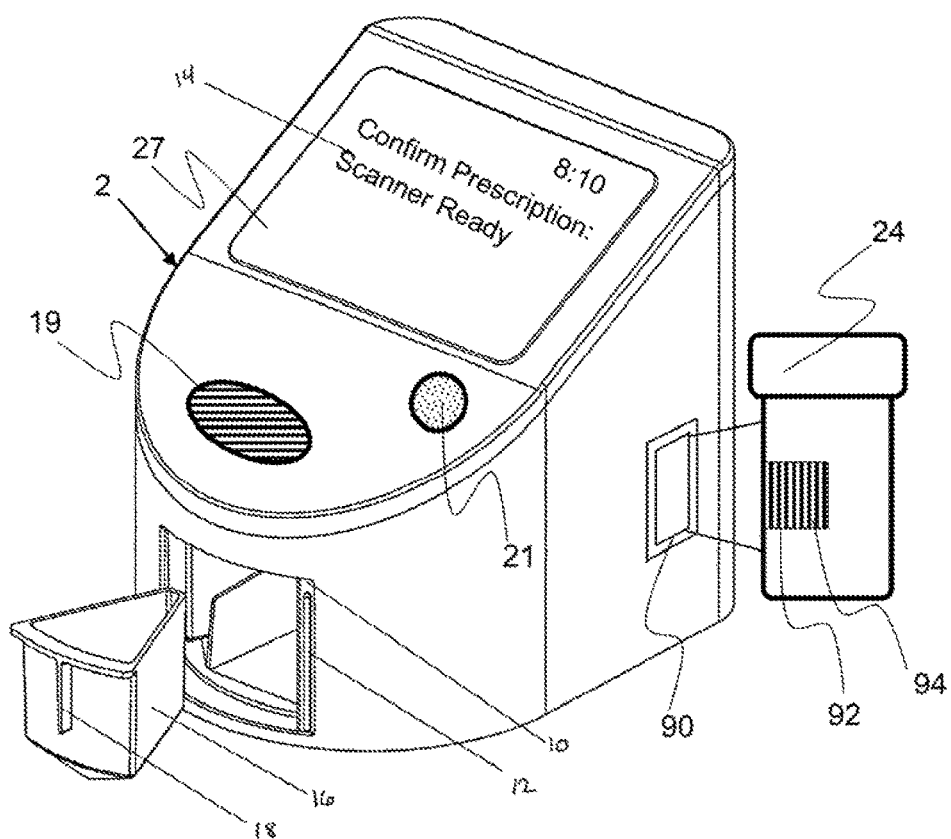

FIG. 11 shows an isometric view of an exemplary pill dispenser having an instruction symbol scanner and a user interface.

Figure 12:
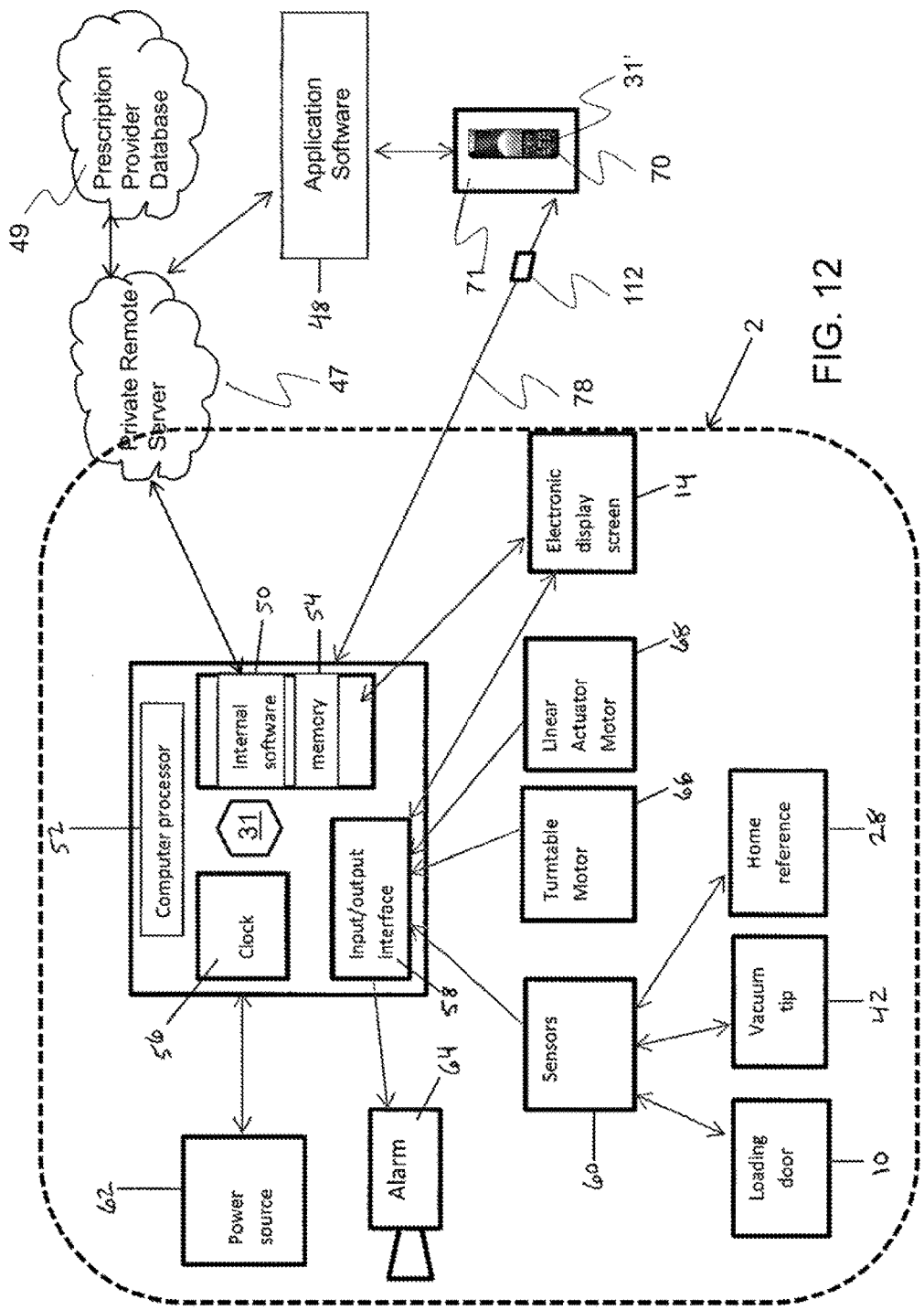

FIG. 12 shows a diagram of the interactions of a pill dispenser system having a remote electronic device for setting dosing regimens.

FIGS. 13-31 show illustrations of exemplary user interface screens of an exemplary pill dispenser system.

Figure 32:
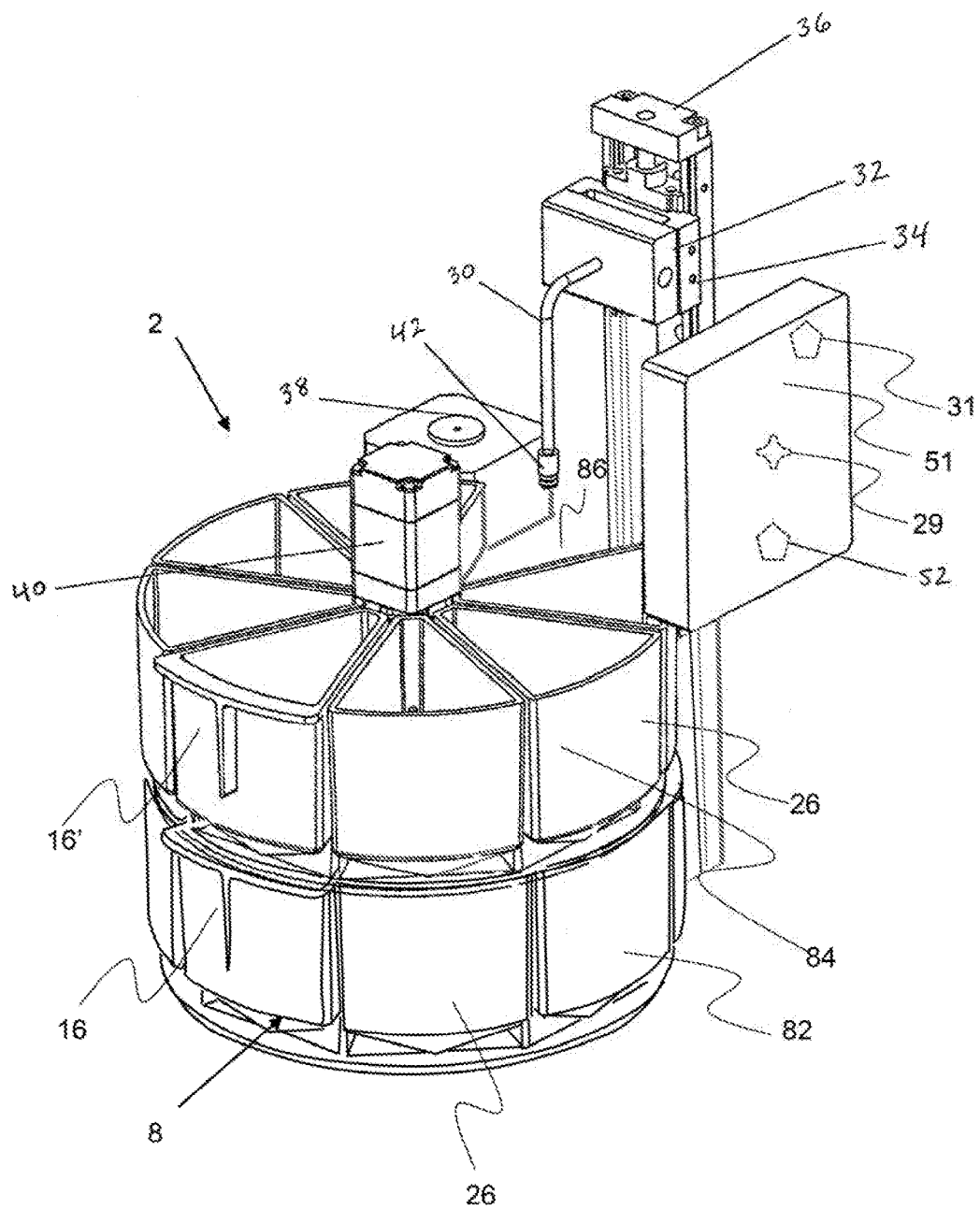

FIG. 32 shows an isometric view of an exemplary pill dispenser having a first and second turntable.

Figure 33:
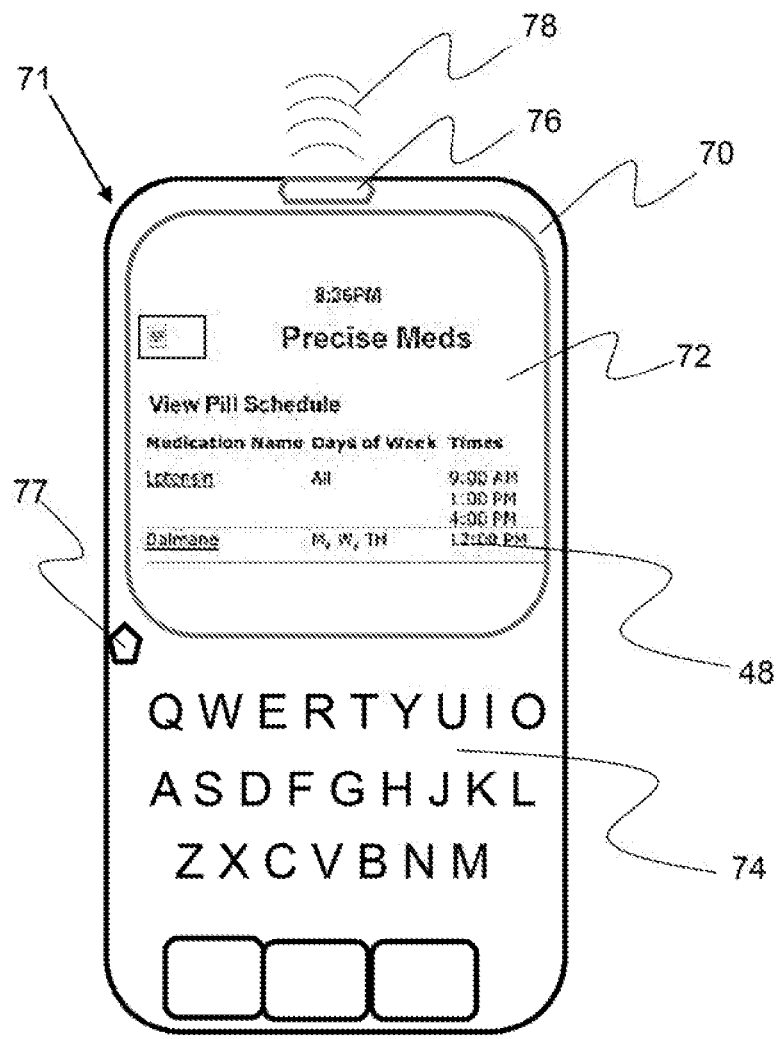

FIG. 33 shows a front view of a remote electronic device having a wireless signal being transmitted therefrom.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale; some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

In cases where, the present specification and a document incorporated by reference include conflicting and/or inconsistent disclosure, the present specification shall control.

Certain exemplary embodiments of the present invention are described herein and are illustrated in the accompanying figures. The embodiments described are only for purposes of illustrating, the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary pill dispenser 2 comprises a cover 4 attached to a base 6 to form an enclosure 23. The enclosure has an opening 25 for removing reservoirs, such as the dispense reservoir 16, as shown. The opening comprises a door 10, having a handle 12. A pill reservoir or dispense reservoir may comprise a reservoir handle 18 for retrieving the reservoir from the pill dispenser. As described, a door 10 may be configured to lock so unwanted access to the pills contained within the enclosure may be prevented. The cover of an enclosure may be affixed to the base to create a continuous outer surface that prevents access. A user may be required to input a password to unlock a door. A user may input a password on a dispenser user interface 27 or on a remote electronic device, not shown. A dispenser user interface may comprise a display screen 14 and any suitable type of user input feature, including one or more buttons, a keyboard, a voice recognition feature, or a touch screen keypad, as shown in FIG. 1. In still another embodiment, a door may be locked until it is time for a dose to be dispensed. A user may confirm that they are ready to, receive the dose and interface with either a remote electronic device or a dispenser user interface to begin transfer of pills from the plurality of pill dispenser reservoirs to a dispense reservoir. In still another embodiment, the door may be locked until a dose is ready, and the door may unlock when a dose of one or more pills is placed in a dispense reservoir at a dose time. For example, a user may have three dose times throughout the day: 8:10 am, 12:30 pm, and 6:00 pm, and the door configured on the pill dispenser may be locked throughout the day except at the dose times. The door may remain unlocked for a pre-set duration, such as one hour and then lock. In another embodiment, the door may unlock at the dose times set by the user and then re-lock after a user has opened the door, taken the dose and closed the door. In addition, a door may be configured to automatically open when a dose is ready or when a confirmation has been provided to a user interface feature. A pill dispenser may be configured with a wireless signal receiver 77 and a wireless signal generator for communication with remote electronic devices such as cellular phones or remote databases. An exemplary pill dispenser may be configured to send alerts to a remote electronic device when a scheduled dose has not been taken for an elapsed period of time. In another embodiment, a user may set a scheduled regimen for a pill loaded into the pill dispenser through a remote electronic device that communicates with the pill dispenser through wireless signals.

As shown in FIG. 2, an exemplary pill dispenser 2 has a plurality of pill reservoirs 26 configured on a turntable 8 and a vacuum manifold 32. The turntable is configured with seven pill reservoirs 26 and one dispense reservoir 16. The turntable may be configured to spin, or rotate, to position a pill reservoir 26" under the vacuum tube 30. A motor 40 may be coupled to the turntable to spin the turntable. A vacuum tube may be configured with a vacuum tip 42 designed to attach to a pill. A vacuum pump 35 may be configured to draw a vacuum to create a suction though the vacuum tube. The tip may comprise an elastomeric material having an opening to draw vacuum, or air, therethrough. A vacuum manifold 34 may be configured with an actuator 34, such as a linear actuator, to move the tube down into a reservoir and up out of a reservoir. An actuator may be driven by a motor 38, pneumatic cylinders or any other conventional means to actuate the vacuum tube up and down. The linear actuator may be coupled to a linear actuator guide 36 as shown. A dispenser control system 29 may comprise one or more dispenser controllers 31, a computer processor 52, a wireless signal receiver 51 and any number of control circuits for controlling the functions of the pill dispenser. The pill dispenser shown in FIG. 2 may be adapted to receive a cover, not shown. A dispenser control system is configured to control the dispensing of pills per the scheduled regimen. The dispenser control system may further comprise the vacuum tube and manifold and turntable control for removing pills from pill reservoirs and placing them in a dispense reservoir. The dispenser control system may be configured to receive commands from a wireless signal and perform physical functions including turning the turntable, opening or unlocking a door, lowering the vacuum tube, turning on and off a vacuum pump to move pills from pill reservoirs to a dispense reservoir as required per dosing regimen. Furthermore, a dispenser control system may receive input from a dispenser user interface to control physical functions. For example, a dispenser control system may receive a password from the user interface and open a door to allow access to a dispense reservoir. A dispenser control system may also comprise any number of sensors to provide feedback as to the position of the turntable and vacuum tube, for example. A sensor may also be configured on the vacuum system or tube to determine the vacuum pressure. When a pill is attached to a vacuum tip, the vacuum pressure may increase above a threshold value, thereby indicating that a pill is attached. If the vacuum pressure drops below the vacuum pressure as the vacuum tube is raised out of a reservoir, the control system may direct the vacuum tube to lower back into the reservoir to retrieve a pill or the turntable may be rotated around or moved back and forth to agitate the pills within the reservoir in an effort to move a pill into a location for attachment to the vacuum tip.

As shown in FIG. 3, an exemplary pill dispenser 2 has a pill reservoir 26 removed from the dispenser enclosure 23 through an opening 25, A prescription pill bottle 24 is shown loading the pill reservoir. Any suitable type of pill, prescription or non-prescription, may be loaded, into a pill reservoir. A single pill type may be simply loaded into a discrete pill reservoir, thereby eliminating the need for manual sorting of pills. The prescription pill being loaded into the pill dispenser is hydrocodone as is shown on the display screen 14. In an exemplary embodiment, a pill may have to be confirmed by a user prior to loading the pill into a pill reservoir. A user may confirm a pill type through a user interface on the dispenser or through a remote electronic device.

As shown in FIG. 4, an exemplary pill dispenser 2 has a plurality of a single type of pills 22 loaded into a pill reservoir 26. The door 10 of the pill dispenser has been closed. The pills are now retained within the enclosure 23. The turntable may be spun by motor 40, as indicated by the large, arrow, to move the pill reservoir 26 under the vacuum tube 30. A sensor 60 is configured to determine the location of the turntable. A tag 81 on pill reservoir 26' may indicate the location of the turntable. A tag may be configured on one or more of the reservoirs or on the turntable to determine the location of the turntable in relation to the vacuum tube. A sensor 60' may be configured on the door to determine if the door is open or closed. This sensor may be used to provide feedback to the control system that a dose has been removed. A sensor 60" may be configured on the turntable to detect if a reservoir is positioned on the turntable. Each reservoir location may have a sensor to determine if the reservoir is properly positioned on the turntable.

Referring now to FIGS. 5A and 5B, an, exemplary pill dispenser 2 has a vacuum tube 30 coupled to a vacuum manifold 32. The pill reservoir 26 has been moved under the vacuum tube 30, whereby the tube vacuum tip 42 may be lowered into the pill reservoir 26 to remove a pill 22 therefrom. Figure 5B shows an enlarged view of a portion of FIG. 5A. The vacuum tube and tip configuration are more clearly shown in FIG. 5B.

As shown in FIG. 6A, an exemplary vacuum tube 30 is coupled to a vacuum manifold 32 and is in a down position within a pill reservoir 26. The vacuum tube 30 has an attached pill 44 coupled to the vacuum tip 42.

As shown in FIG. 66, the vacuum tube 30 has an attached pill 44 coupled to the vacuum tip 42. The linear actuator 34 has moved the vacuum manifold 32 into a down position, whereby the vacuum tip 42 may couple with a pill 22. The pill reservoirs may be configured with a sloped bottom surface, as shown, to direct the pills to a suitable location for attachment to the vacuum tip.

As shown in FIG. 7A, an exemplary vacuum tube 30 is in an up position over a pill reservoir 26 with an attached pill 44, coupled thereto. FIG. 7B shows an expanded view of the tube in FIG. 7A with the attached pill 44 coupled to the vacuum tip 42.

As shown in FIG. 8, an exemplary pill dispenser 2 has a vacuum tube 30 in an up position over a dispense reservoir 18. The attached pill 44 from the pill reservoir 26 is now ready for placement in the dispense reservoir 16. The turntable 8 has been spun to locate the vacuum tube with pill attached over the dispense reservoir. The vacuum tube may be lowered into the dispense, reservoir and the attached pill 44 may be placed into the dispense reservoir. In another embodiment, the vacuum tube may simply release the attached pill 44 into the dispense, reservoir.

As shown in FIG. 9, the exemplary pill dispenser 2 has the turntable 8 configured with the dispenser reservoir 16 aligned with the door location 10. The dispense reservoir contains a dose pill 46. It is to be understood that any number of dose pills may be placed in the dispense reservoir from any of the plurality of pill reservoirs to provide a dose 80. A dose may be one or more pills removed from and placed into the dispense reservoir.

As shown in FIG. 10, an exemplary pill dispenser 2 has a dispense reservoir 16 removed from a dispenser opening 25. The door 10 has been opened and the dispense reservoir has been removed by means of the dispense handle 18. The display screen 14 indicates the contents of the dose, or pill, contained within the pill dispenser.

As shown in FIG. 11, an exemplary pill dispenser 2 has an instruction symbol scanner 90 and a dispenser user interface 27. A user may confirm a prescription to be loaded by scanning an instruction symbol 92, or bar code 94 for example, on a prescription pill bottle 24 or prescription packaging with an instruction symbol scanner 90. A bar code may be printed on a label or other packaging material when a prescription is retrieved from a pharmacy, for example. An instruction symbol scanner may be configured on the pill dispenser or a remote electronic device. In an, exemplary embodiment, a prescription pill cannot be loaded into the pill dispenser or into a pill reservoir until the prescription is confirmed by a user interface. In another embodiment, a user may input a prescription number, or other code associated with the prescription, into a user interface to confirm the prescription to be loaded. A user may input a prescription number or conformation code into a dispenser user interface 27, or a remote electronic device user interface, not shown.

FIG. 11 also shows a speaker 19 and light 21 configured to provide an alarm to alert a user that a dose is ready. A speaker may also be configured to verbally alert a user that a dose is ready, or to prompt a user during a user interface. For example, a speaker may be used to state "confirm prescription, scanner ready", whereby the user is directed to scan an instruction symbol with the instruction symbol scanner. Any number of verbal commands or prompts are envisioned to facilitate use of the pill dispenser or pill dispenser system. A tight 21 may flash or illuminate when a dose is ready. The display screen may also display instructions, such as that a dose is ready.

As shown in FIG. 12, an exemplary pill dispenser system may connect, via a wireless signal 78, with a remote electronic device 71, such as a mobile phone 70 to receive data-files 112 and/or for setting dosing regimens. The remote electronic device 71 utilizes an application software program 48 which may reside, at least partially, on a private remote server 47 or database 49. As shown in HG, 12, the private remote server 47 interfaces with a prescription provider database 49, A dispenser controller 31 is configured within the pill dispenser 2, as indicated by the dashed line, to control functions of the dispenser and a second dispenser controller 31' is configured on the remote electronic device and may be used to input dosing times, for example.

In an exemplary embodiment, when a user receives a prescription from a prescription pill provider, information related to that prescription may be transferred from the database 49 to a private remote server. When a user logs into the application software program 48 through the remote electronic device 71 the dosing regimen and prescription identification, for example, may automatically be updated in the application software 48. The application software program 48 then utilizes the updated dosing regimen and prescription identification to set specific dose times for a prescription pill, and/or in some cases to confirm the prescription identification before loading into the pill dispenser. A user may interface with the application software on the mobile phone 70 to control functions of the pill dispenser by transmission of a wireless signal. The mobile phone is therefore configured with a dispenser controller 31' that may be an application software.

An application software program may have any number of sub-programs or features to enable a user to view prescription status, pill dispenser status, set or change dosing times, input or load prescription and non-prescription pills into the pill dispenser, alert the user of dosing time, provide a report on compliance, alert an alert contact if one or more doses are not taken and the like. These and other software features are described herein. The user interface screens shown in FIGS. 13-31 may be configured on a dispenser user interface or on a remote electronic device.

Figure 13:
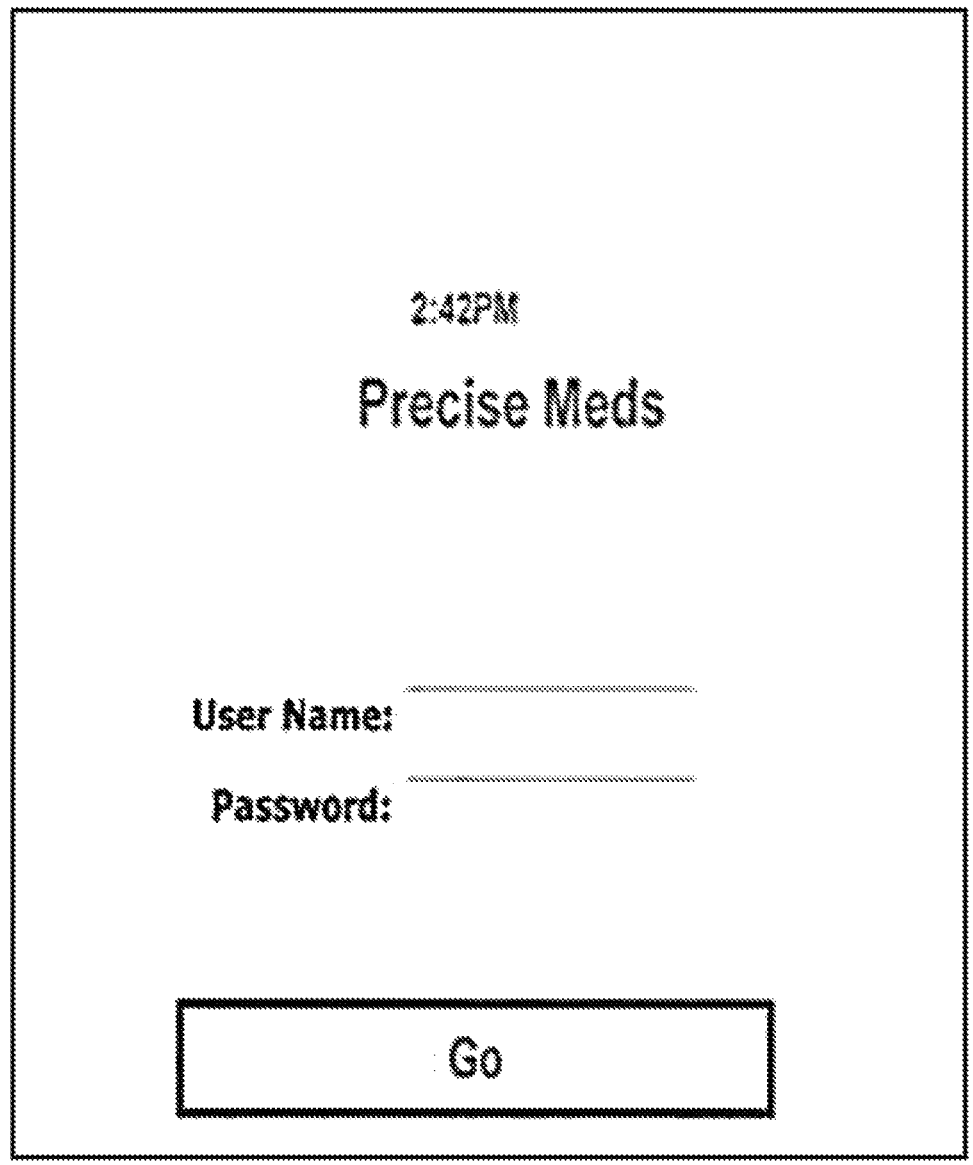

As shown in FIG. 13, a user interface, on a remote electronic device for example, comprises a user login feature, whereby a user is prompted to input a user name and password.

Figure 14:
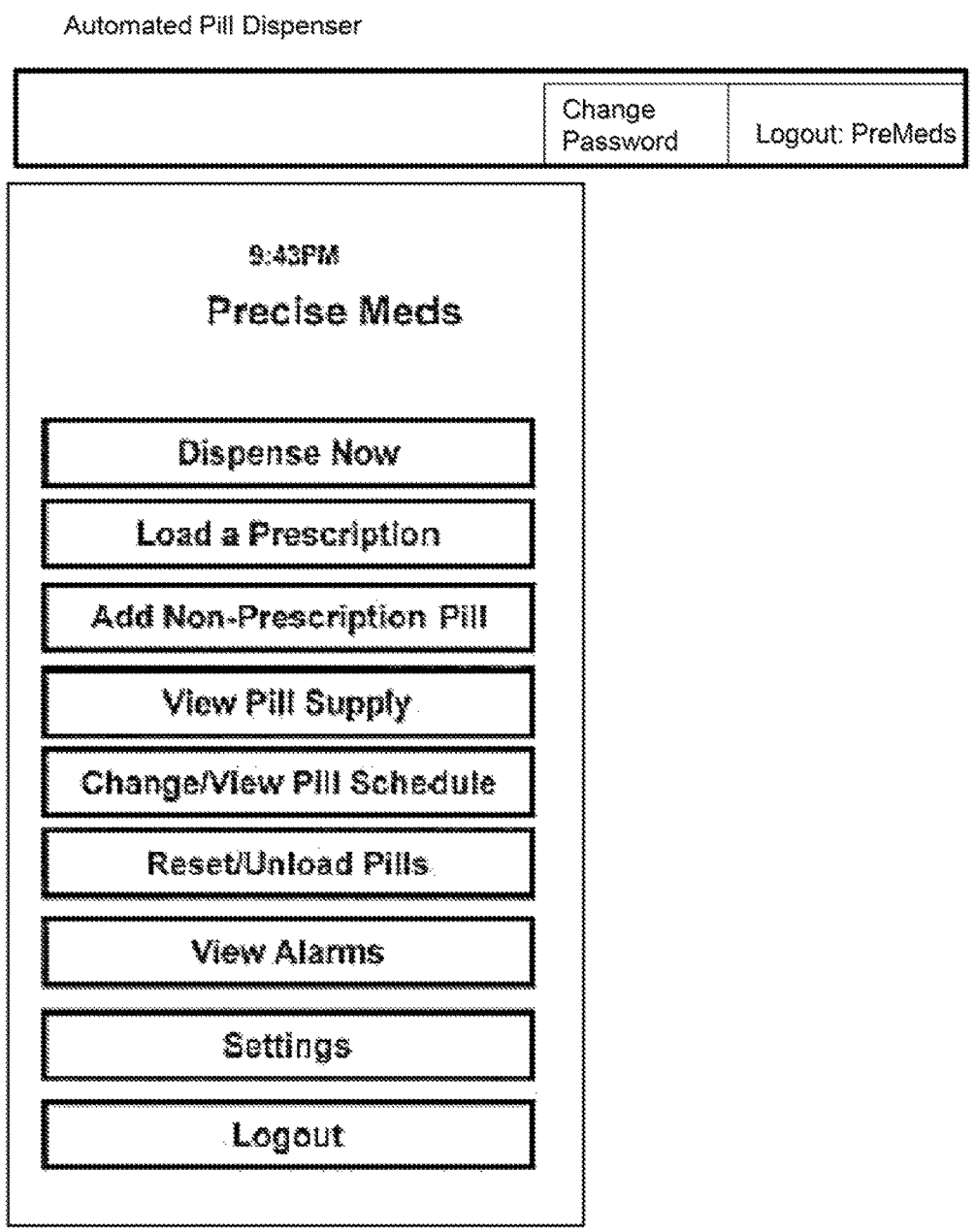

As shown in FIG. 14, a user interface, on a remote electronic device for example, comprises a menu screen or display having a list of sub-programs or features. As shown in FIG. 14, the application software program comprises "dispense now", "load a prescription", "add non-prescription pill", "view pill supply", "change/view pill schedule", "reset/unload pills", "view alarms", "settings" and "logout and/or login" sub-programs.

Figure 15:
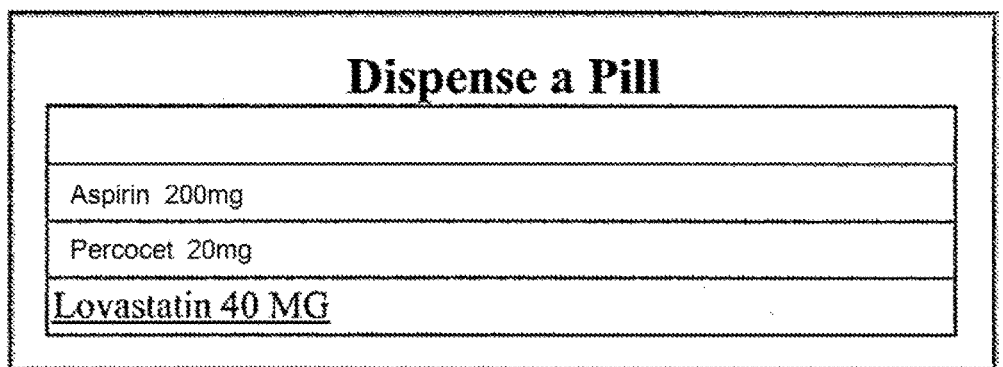

As shown in FIG. 5, a user interface, on a remote electronic device for example, comprises a "dispense now" sub-program that may be used to direct the pill dispenser to dispense one or more pills contained within the pill dispenser. The "dispense now" sup-program may only allow dispensing of pills that are prescribed as "take as needed" or non-prescription pills. This feature helps to ensure proper compliance with prescription regimens. The dispenser control system may be configured to only show pills that are "take-as-needed" to be displayed in the "dispense now" sub-program. As shown in FIG. 15, aspirin and Percocet are shown as options for dispense now. A user may select one or more dispense now pills displayed to have the pills dispensed.

As shown in FIG. 16, a user interface, on a remote electronic device for example, comprises a "load a prescription" sub-program. The "load a prescription" sub-program may show prescriptions that have been picked up from a prescription provider that are ready to be loaded into the pill dispenser. As shown a plurality of pills are ready for loading. A user may select one of the prescriptions and then be prompted by the remote electronic device and/or pill dispenser to load the selected pill. The pill dispenser may then identify a specific pill reservoir for receiving the selected prescription pill. In some embodiments, as described herein, a prescription, pill may have to be confirmed by a user inputting a pill or prescription identifier. A user may have to input a prescription number or scan an instruction symbol with a remote electronic device or with the pill dispenser.

As shown in FIG. 17, a user interface display comprises a dose time input feature for a pill to be loaded into the pill dispenser. A user may select what days of the week and times of day for the pill to be dispensed. If the selected number of days does not match the dosing regimen received from the prescription pill provider, then an error message will appear. For example, if the dosing regimen indicates to take the prescription pill three times a week you will receive an error message unless the scheduled regimen input matches the dosing regimen of three times per week. A compliance feature of the dispenser control system may only allow selection of compliant dose times or may only display dose times that are compliant for selection.

As shown in FIG. 18, a user interface, on a remote electronic device for example, comprises a dose time input feature for a pill to be loaded into the pill dispenser. The times of day for dosing is displayed based on the dosing regimen received from the prescription pill provider. For example, if the dosing regimen indicates to take the prescription pill once a day then only one scrolling time feature will be displayed in the 'Set Schedule List' for a pill to be loaded into the pill dispenser. A scrolling time input feature may allow a user to scroll the time and then select a time of day. A 'Current Schedule List' is displayed which shows all times for the loaded prescriptions whose days of the week matche the prescription being scheduled. Two default times that have been preset by the user are also shown under the current schedule list for selection by the user. This allows the user to select the same scheduled time as other prescriptions so that they may take prescriptions at the same time. A 'Default Schedule List' may also be included when presetting the hours of day the user would like to take their pills. This may be included in the "default times" sub-program.

As shown in FIG. 19, a user interface on a remote electronic device comprises a "load a prescription" sub-program with a confirmation screen to confirm the user is ready for loading of a pill.

As shown in FIG. 20, a user interface, on a remote electronic device for example, comprises an "add non-prescription pill" sub-program that provides an input for a pill name, recurrence and interval. A user may select the days of the week and time of day they want the non-prescription pill to be dispensed. A user may also select default times as previously described.

As shown in FIG. 21, a user interface comprises a "view pill supply" sub-program that displays the name of pills loaded in the pill dispenser and the quantity remaining. A user may select one of the loaded pills, DiaVan 320 for example, and a more detailed display may be provided, as shown in FIG. 22. FIG. 22 shows a display of information related to the prescription pill, DiaVan 320, loaded into the pill dispenser. The prescription number, medication name, generic name, number of pills remaining, refill quantity, until date, and load date are displayed. The "until date" is the date the pills will run out based on the dosing regimen. The "load date" is the date the prescription was loaded into the pill dispenser. In addition, prescription instructions, warnings and side effects may be displayed to a user.

As shown in FIG. 23, a user interface, on a remote electronic device for example, comprises a "change/view pill schedule" sub-program that displays and/or allows a user to change a schedule, or dosing regimen for pills loaded into the pill dispenser. A user may select a pill from the display, as shown in FIG. 23 and change a dosing time.

Figure 25:
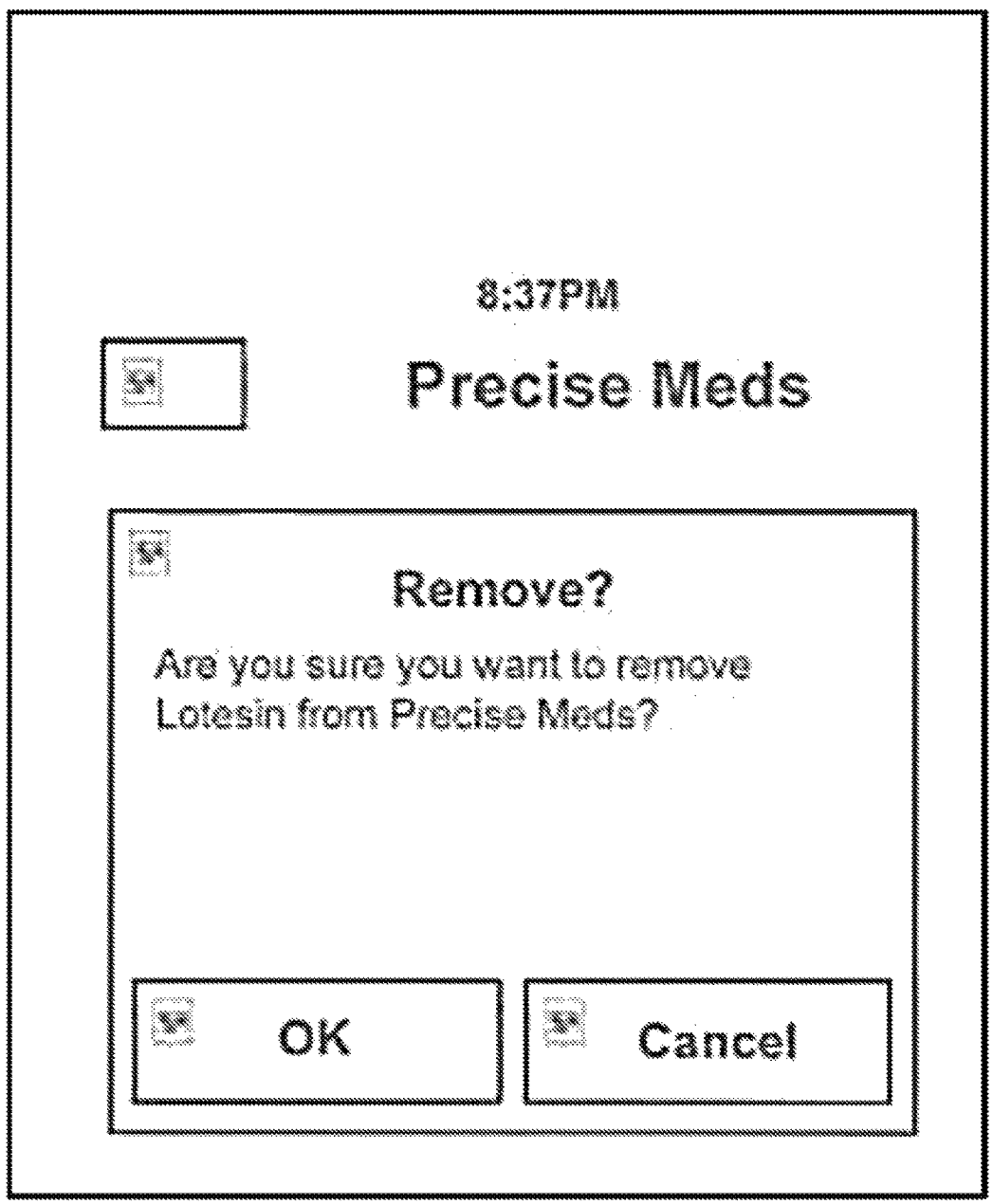
Figure 26:
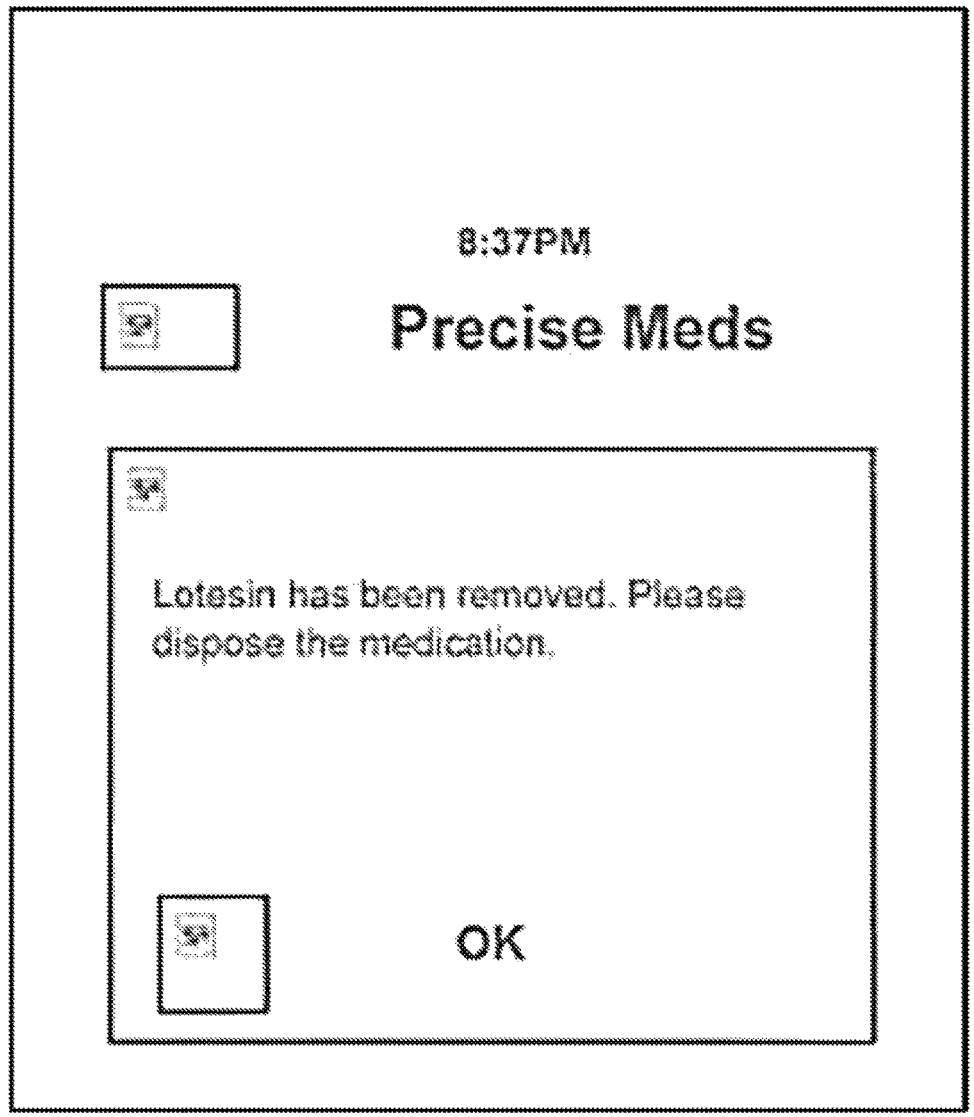

As shown in FIG. 24, a user interface comprises a "reset/unload pills" sub-program that provides a user with an interface for unloading pills from the pill dispenser. A user may select a pill to remove from the dispenser, as shown in FIG. 24, whereby a user may select a loaded pill and then be prompted to remove the pill, as shown in FIG. 25. The pill dispenser may be directed to align the pill reservoir containing the selected pill for removal with an opening. A user may then remove the selected pills from the pill reservoir, and replace the pill reservoir. A confirmation may, be displayed, as shown in FIG. 26, that the selected pill for removal has been removed from the pill dispenser.

Figure 27:
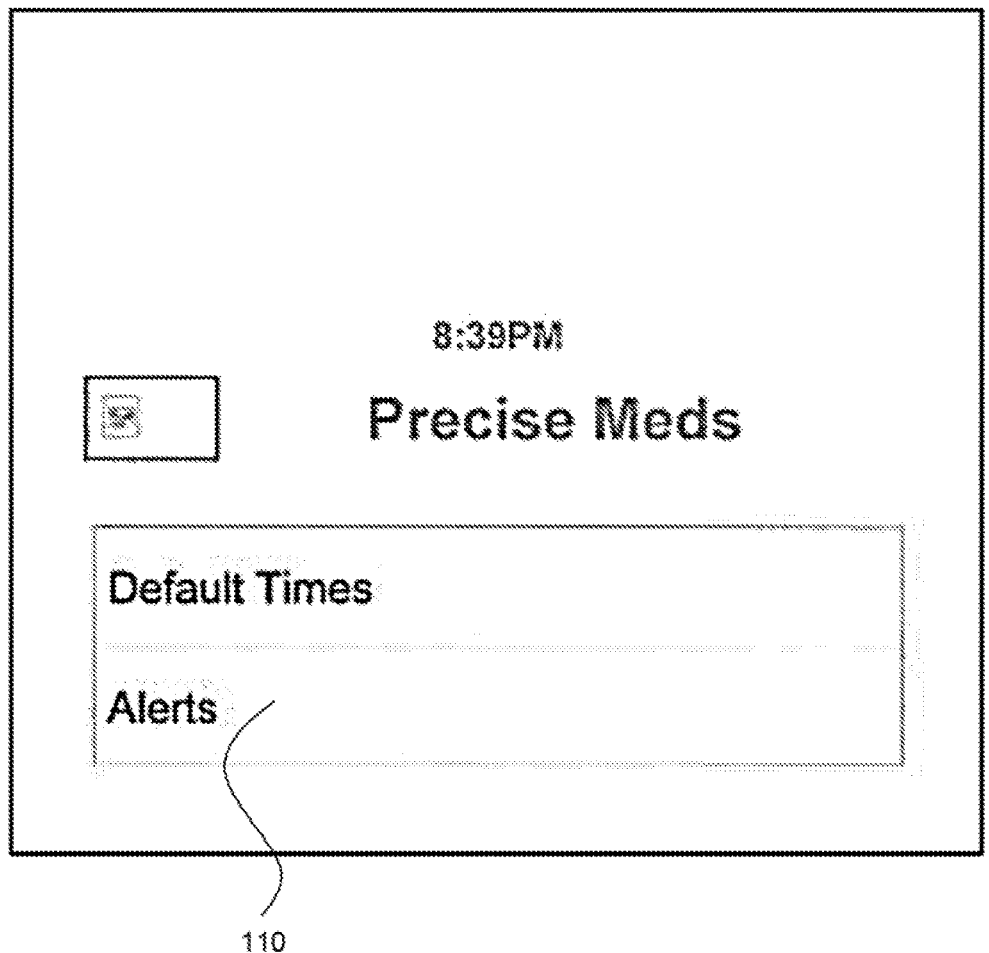
Figure 28:
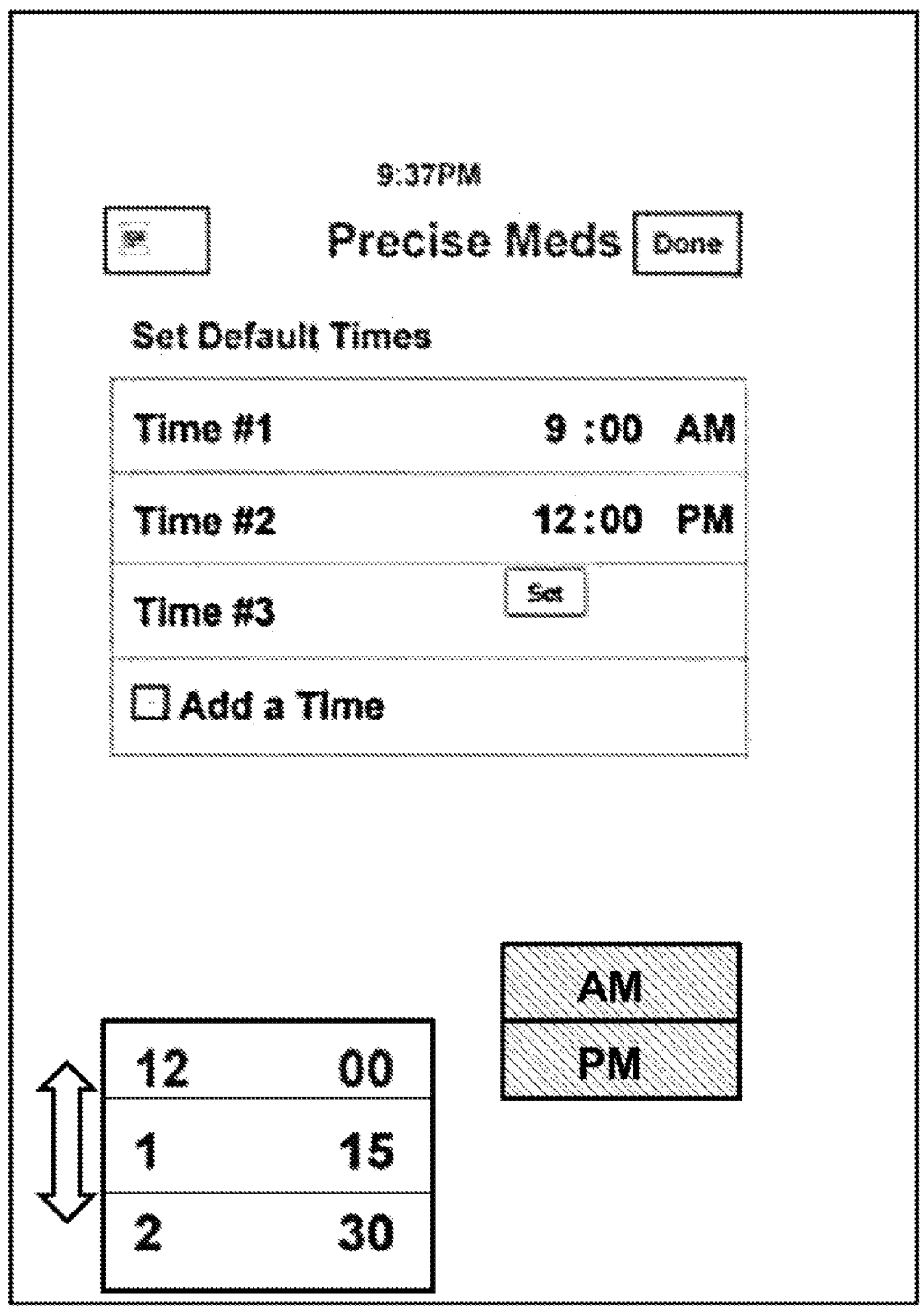

As shown in FIG. 27, a user interface comprises a "settings" sub-program that enables a user to input and/or change default times, or alert durations and alert contacts. The "alert" sub-program 110, allows a user to select when and how alerts are to be made. As shown in FIG. 27, a user may be prompted to select default time or alerts. A user may select default times and change or input a new default time as shown in FIG. 28. Default times are times of day when a dose will be provided. As shown in FIG. 28, a scroll feature, as indicated by the double arrow, may allow a user to quickly scroll time to select a desired default time.

Figure 29:
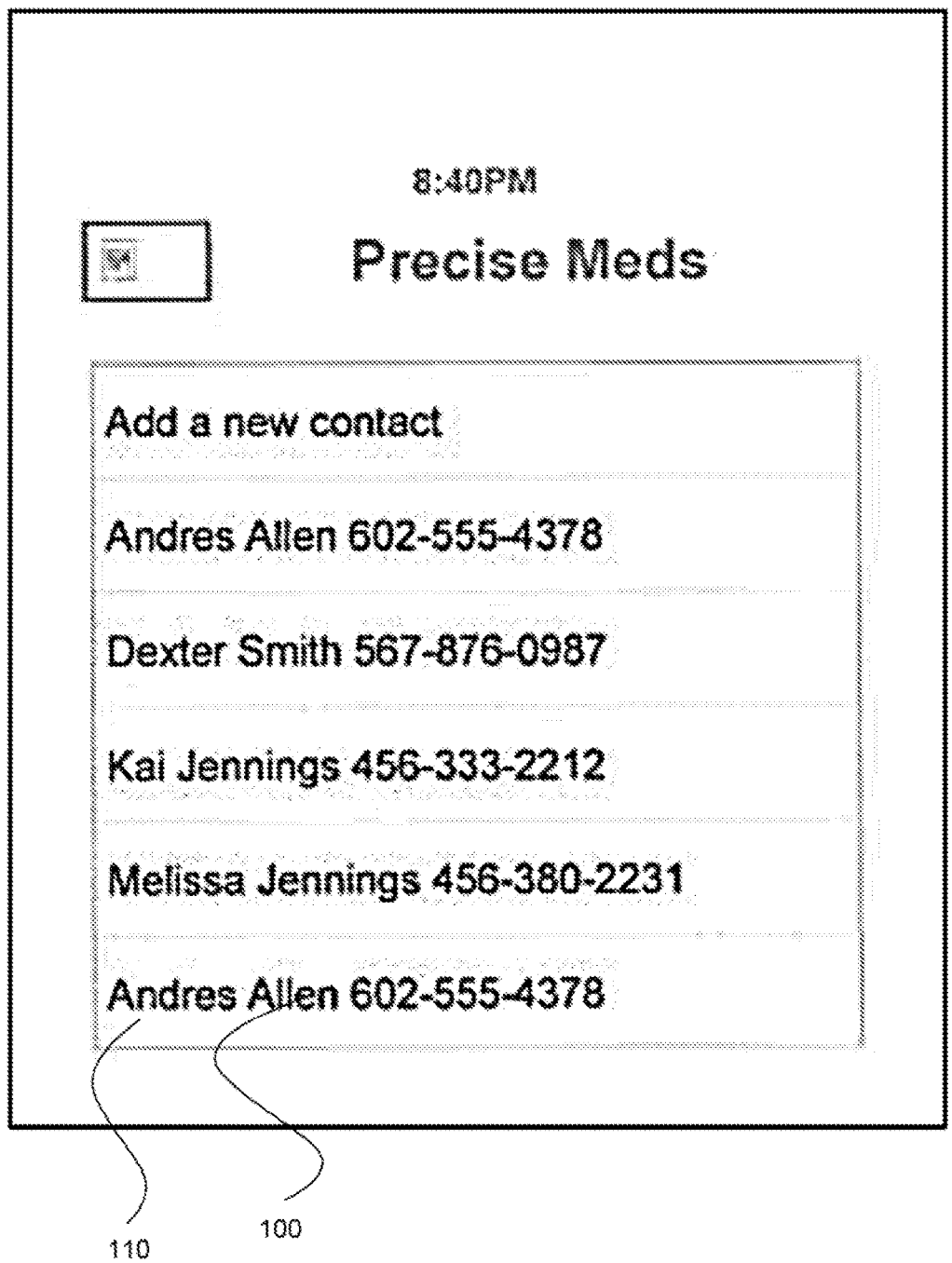
Figure 30:
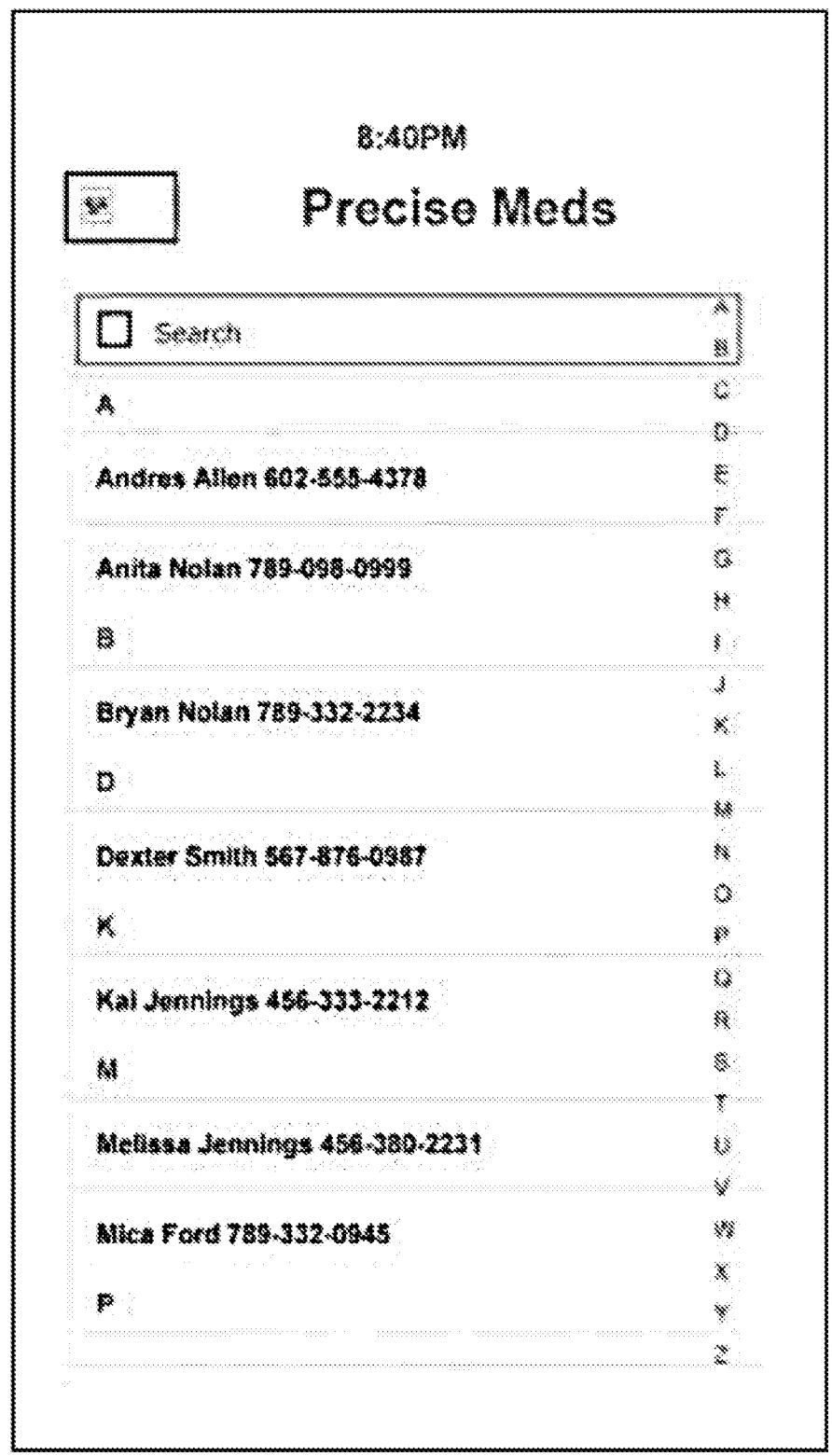
Figure 31:
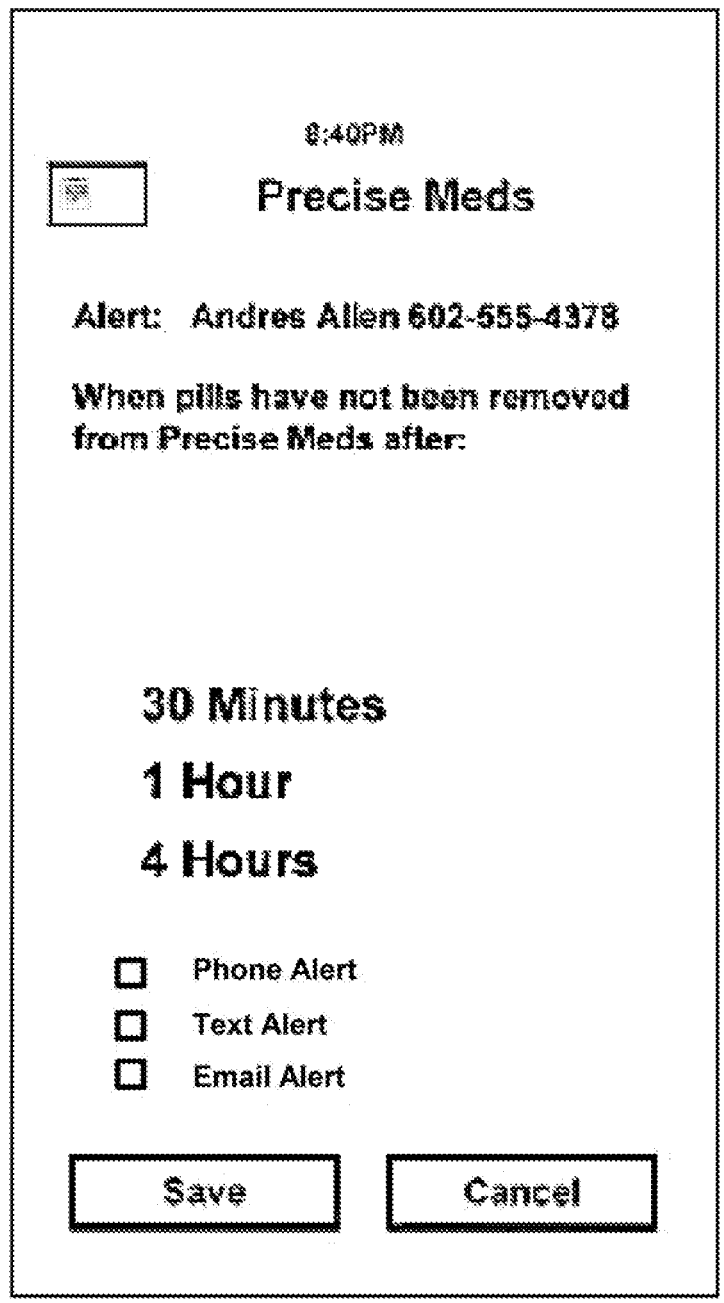

As shown in FIG. 29, an "alert" subprogram 110, may enable a user to select one or more alert contacts 100. An alert contact is a person that will be alerted if a dose in not taken within an alert set time duration. An alert notification may be a text message, email or phone call to the user and/or one or more alert contacts after a set time has elapsed from a scheduled dose being missed. A user may select an alert contact from a contacts list on the remote electronic device, or add a new contact. A user may select how an alert contact will be alerted, such as by phone, text message and/or email. FIG. 30 shows that a user may search and select one or more alert contacts from an existing contact list on their remote electronic device, FIG. 31 shows an alert duration input display. A user may select an alert duration, as shown, and then select an alert method: phone alert, text alert and/or email alert.

As shown in FIG. 32, a pill dispenser 2 has a first turntable 82 configured under a second turntable 84. The second, or upper, turntable may be configured with a turntable opening 86, whereby the vacuum tube 30 can be lowered down into a reservoir of the first turntable. A turntable opening may be a location on the second turntable without a reservoir. The first turntable may comprise only pill reservoirs, or some combination of pill and dispense reservoirs. Likewise, the second turntable may comprise only pill reservoirs, or some combination of pill and dispense reservoirs. In an exemplary embodiment, a dispenser opening is configured to allow access to pill and/or dispensing reservoirs, configured on the first turntable. In another embodiment, a dispenser opening is configured to allow access to reservoirs, pill and/or dispensing, configured on the second turntable. For example, a first turntable may consist of pill reservoirs, and the second turntable may comprise pill reservoirs and a dispense reservoir, whereby pills from pill reservoirs configured on the first turntable are dispensed into the dispense reservoir configured, on the second turntable.

As shown in FIG. 33, a remote electronic device 71 is a mobile phone 70 having a, wireless signal receiver and wireless signal generator 76 that is transmitting a wireless signal 78. The user may use the remote user interface 74, to send commands through a wireless signal to a pill dispenser, as described herein, The display screen 72 is displaying one user input display from the application software program 48. The remote electronic device may interface with a prescription provider database to receive information regarding prescription medication that are in or are to be loaded in the pill dispenser.

The remote electronic device may send commands to the pill dispenser to direct it to perform physical functions. A pill dispenser may have a control system that is only configured to perform physical functions or only physical function as directed by a remote electronic device. All the scheduling functions including setting dosing time as described may be accomplished through the application software program on a remote electronic device.

A dosing regimen for a pill may include the quantity of pills, and number of doses per day to take the medication. For example, a dosing regimen may be for example, take three times daily. The dosing regimen may be loaded on the application software program automatically from the database and not allow the user to change the number of pills and number of dose per day.

A dosing schedule is the particular times of day and quantity of pills that are scheduled to be dispensed to a user by the pill dispenser.

The dispensing and pill reservoirs are configured to hold a plurality of loose pills. A user may simply pour a number of pills into a pill dispenser. A reservoir may have any suitable volume including, but not limited to, about 5 cc or more, about 10 cc or more, about 25 cc or more, about 50 cc or more about 100 cc or more and any range between and including the volumes provided. A pill or dispense reservoir may be configured to hold any number of loose pills including, but not limited to one or more, two or more, five or more, ten or more, twenty or more, fifty or more and any quantity between and including the number of pills listed.

A dispenser controller, as used herein, is configured to provide instruction and commands to the pill dispenser to control the functions of the pill dispenser. A dispenser controller may comprise a microprocessor or any other suitable electronic logic device. A dispenser controller may be configured on a pill dispenser and/or a remote electronic device. In an exemplary embodiment, a dispenser controller is configured on a pill dispenser for controlling scheduled functions, such as dispensing and loading. In another exemplary embodiment, a dispenser controller is configured on a remote electronic device and is used for inputting a scheduled regime. Any combination of dispensing controllers may be used.

A compliant dosing regimen is a scheduled regimen that complies with a dosing regimen that may be provided by a prescription pill provided, for example. A prescription pill provider may provide a dosing regimen through any suitable manner to the pill dispenser system including, a data-file provided from a database or an application software, or through an identification code on the prescription pill bottle or packaging, for example. In an exemplary embodiment, the pill dispenser system ensures that a scheduled regimen, either input or verified by a user, is compliant with a dosing regimen.

A dosing input feature may be a display screen and user interface that is configured on the pill dispenser or on a remote electronic device. A user may interface with the dosing input feature to input a scheduled regimen for a pill loaded into the pill dispenser.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A pill dispenser system comprising:
   a) a pill dispenser comprising:
      i) an enclosure for retaining a plurality of pills;
      ii) a door to the enclosure that opens to provide access to a dose comprising one or more pills dispensed by said pill dispenser;
         wherein the door is locked to prevent access to said dispensed pill;
      iii) a sensor configured to sense a position of the door;
         wherein the sensor senses when the door is open and wherein the dose is confirmed when the door is closed after retrieval of the dose
      iv) a signal receiver for receiving a data from a prescription provider comprising:
         a pill identification for a pill; and
         a pill dosing regimen for said pill;
         wherein the signal receiver receives the data from a remote source;
         wherein a pill dosing regimen is a schedule that defines the quantity of said pill
         and times for said pill to be taken;
   b) a dispenser controller having a dispenser software program;
   c) a pill confirmation feature comprising:
      i) a pill identifier input feature configured for a user to provide a pill identifier to the pill dispenser system;
         wherein the pill identifier input feature comprises an instruction symbol scanner configured to read an instruction symbol, having a pill identifier, on a prescription pill container; and
         wherein the pill confirmation feature confirms that said pill identifier matches
      said pill identification received by said signal receiver from the prescription provider and is a scheduled pill having a received pill dosing regimen before said pill is loaded into said enclosure;
   d) a user interface configured for inputting a scheduled regimen for a pill loaded into said enclosure;
   e) a plurality of pill reservoirs; and
   f) a dispense reservoir for receiving one or more pills from the one of more of the plurality of pill reservoirs to produce a dose;
      wherein the user interface comprises a remote electronic device and a dispenser user interface on the pill dispenser, and
      wherein the pill dispenser system comprises a dispenser control system;
      wherein the remote electronic device is used to input the scheduled regimen for a pill loaded into said enclosure;
      whereby a dosing command to dispense said pill from said plurality of pill reservoirs to said dispense reservoir is provided by a wireless signal from said remote electronic device to the dispenser control system; and
      wherein a dosing command to dispense said pill from said plurality of pill reservoir to said dispense reservoir is confirmed by a user interfacing with said dispenser user interface to open the door to release the dispense reservoir.

2. The pill dispenser system of claim 1, further comprising an alert sub-program configured to send an alert notification to an alert contact when a-scheduled dose is not retrieved within an elapsed period of time from a scheduled dose time; wherein the elapsed time is measure from the scheduled dose time to the time the door is closed after removal of the dose reservoir; wherein the alert sub-program comprises an input, through said user interface, for one or more alert contacts to receive the alert notification.

3. The pill dispenser system of claim 2; wherein the alert notification of the alert sub-program is a wireless signal received by one of said input alert contacts, on said an alert contacts remote electronic device.

4. The pill dispenser system of claim 1, wherein the pill dispenser comprises a pill reservoir opening and a plurality of pill reservoirs for retaining pills, wherein one of said plurality of said pill reservoirs cannot be removed from the opening until the pill confirmation feature confirms that said pill identifier matches said pill identification data that was previously received by said signal receiver from said prescription provider.

5. A pill dispenser system comprising:
a) a pill dispenser comprising:
  i) an enclosure for retaining a plurality of pills;
  ii) a door to the enclosure that opens to provide access to a dose comprising one or more pills dispensed by said pill dispenser;
    wherein the door is locked to prevent access to said dispensed pill;
  iii) a sensor configured to sense a position of the door, wherein the sensor senses when the door is open and wherein the dose is confirmed when the door is closed after retrieval of the dose:
  iv) a signal receiver for receiving a data from a prescription provider comprising:
    a pill identification for a pill; and
    a pill dosing regimen for said pill;
    wherein the signal receiver receives the data from a remote source;
    wherein a pill dosing regimen is a schedule that defines the quantity of said pill
and times for said pill to be taken;
b) a dispenser controller having a dispenser software program,
c) a pill confirmation feature comprising:
  i) a pill identifier input feature configured for a user to provide a pill identifier to the pill dispenser system:
    wherein the pill identifier put feature comprises an instructions symbol
    scanner configured to read an instruction symbol, having a pill identifier, on a prescription pill container; and
    wherein the pill confirmation feature confirms that said pill identifier matches
    said pill identification received by said signal receiver from the prescription provider and is a scheduled pill having a received pill dosing regimen before said pill is loaded into said enclosure:
d) a user interface configured for inputting scheduled regimen for a pill loaded into said enclosure;
e) a plurality of pill reservoirs; and
f) a vacuum manifold and vacuum tube having a collection tip configured to attach to a pill; wherein said vacuum manifold is configured to remove a pill from one of said plurality of pill reservoirs and place said pill in a dispense reservoir to produce said dose in the dispense reservoir; wherein the pill dispenser is configured to provide a plurality of different pills to said dispense reservoir from said plurality of pill reservoirs;
wherein the vacuum manifold is configured to lower said vacuum tube down into one of the plurality of pill reservoirs to remove a pill from one of said plurality of pill reservoirs, and subsequently raise said vacuum tube, with a pill attached thereto, above one of said plurality of pill reservoirs.

6. The pill dispenser system of claim 5, wherein the plurality of pill reservoirs are configured on a turntable, whereby the turntable is configured to rotate said plurality of pill reservoirs to locate one of said plurality of pill reservoirs under the vacuum manifold and the vacuum tube;
wherein the vacuum manifold is configured to lower said vacuum tube down into one of the plurality of pill reservoirs to remove a pill from one of said plurality of pill reservoirs, and subsequently raise said vacuum tube, with a pill attached thereto, above one of said plurality of pill reservoirs; wherein the turntable is configured to rotate and locate the dispense reservoir under the vacuum tube having a pill attached thereto;
whereby said vacuum tube is configured to release said pill into said dispense reservoir; and wherein a plurality of different pills from the plurality of pill reservoirs are released into the dispense reservoir to create a dose; and
wherein the turntable is configured to rotate and locate the dispense reservoir under the vacuum tube having a pill attached thereto, whereby said vacuum tube is configured to release said pill into said dispense reservoir.

7. The pill dispenser system of claim 5,
wherein the pill dispenser is configured to remove a plurality of pills from the plurality of pill reservoirs to provide a dose comprising at least two different pills, from at least two different pill reservoirs, into the dispense reservoir per the scheduled regimen.

8. The pill dispenser system of claim 1, wherein the signal receiver is a wireless signal receiver and the remote source is a remote electronic device.

9. The pill dispenser system of claim 1, wherein the signal receiver is a wireless signal receiver and the remote source is a prescription provider database and the pill is a prescription pill.

10. The pill dispenser system claim 1, wherein the instruction symbol is a bar code.

11. The dispensing pills of claim 1, wherein the instruction symbol is a QR symbol.

12. The pill dispenser system of claim 1, wherein the user interface comprises a remote electronic device.

13. The pill dispenser system of claim 1, wherein the user interface displays to a user, a dosing regimen that is compliant with said pill dosing regimen received by the signal receiver and wherein a dosing compliance feature requires a user to input a scheduled regimen that is a compliant dosing regimen.

14. The pill dispenser system of claim 1, wherein the user interface comprises a remote electronic device and wherein a dosing regimen that is compliant with said pill dosing regimen received by the signal receiver is displayed on said remote electronic device, and wherein a user inputs a scheduled regimen that is a compliant dosing regimen through said remote electronic device.

* * * * *